United States Patent [19]
Nelson et al.

[11] Patent Number: 5,633,711
[45] Date of Patent: May 27, 1997

[54] MEASUREMENT OF MATERIAL PROPERTIES WITH OPTICALLY INDUCED PHONONS

[75] Inventors: Keith A. Nelson, Newton; Anil R. Duggal, Arlington; John A. Rogers, Cambridge, all of Mass.

[73] Assignee: Massachusettes Institute of Technology, Cambridge, Mass.

[21] Appl. No.: 350,378

[22] Filed: Dec. 5, 1994

Related U.S. Application Data

[63] Continuation of Ser. No. 910,762, Jul. 8, 1992, abandoned, which is a continuation-in-part of Ser. No. 726,759, Jul. 8, 1991, abandoned.

[51] Int. Cl.$^6$ .............................. G01J 3/30; G01N 21/00
[52] U.S. Cl. .............................. 356/318; 356/432; 73/655
[58] Field of Search .............................. 356/318, 432 T, 356/432; 73/655

[56] References Cited

U.S. PATENT DOCUMENTS 4,522,510  6/1985  Rosencwaig et al. .
4,728,165  3/1988  Powell .

OTHER PUBLICATIONS

Barish, *J. Ken. Physics*, 85(7), 1 Oct., 1986, p. 4194.
Burzynski et al. *Polymer*, 1989, vol. 30, Jul., p. 1247.
Deeg, *IEEE Journal of Quantum Electronics*, vol. QU–22, No. 8, Aug. 1986, p. 1476.
Duggal, "Picosecond–Microsecond Structural Relaxation Dynamics in Polypropelyne Glycol" Journal of Chemical Physics No. 94 pp. 7677–7688, Jun. 15, 1991.
Espinet, *Appl. Phys. Lett.*, vol. 50, 26, 29 Jun. 1987, p. 1925.
Fishman, "Surface Selectivity in Holographic Transient Grating Diffraction" Sep. 1991 Journal of the Optical Society of America, B8 pp. 1880–1888.
Greene, *Chemical Physics Letters*, vol. 139, No. 5, 4 Sep. 1987, p. 381.
Meth, *Chemical Physical Letters*, vol. 162, 4, 5, 20 Oct. 1989, p. 306.
Nelson, *J. Appl. Phys.*, 53 (2), Feb. 1982, p. 1144.
Noll, *Journal of Non–Crystal and Solids*, 97 and 98 (1987) 141–144 No Month Available.
Portella, *Journal of Physical Chemistry*, vol. 91, No. 14, Jul. 1, 1987, p. 3715.
Prasad, *Thin Solid Films*, 152 (1987) 275 No Month Available.
Rao, *Appl. Phys. Lett.*, 48 (18), 5 May 1986, p. 1187.
Rao, *Appl. Phys. Lett.*, 6, 10 Feb. 1986, p. 387.
Rao, *Macromolecules* 1989, 22, 085.
Rose, *Chemical Physics Letters*, vol. 106, 1, 2, 13 Apr. 1984, p. 3.
Rothenhausler, *Thin Solid Films*, 159 (1988) p. 323 No Month Available.
Meth. *J. Appl. Phys.*, 67:7 (1990) No Month Available.
Rogers et al., "Real–Time In Situ Characterization of Thin Films", CHEMF., 8, 27 (1992), pp. 4–8 No Month Available.
Duggal et al., "Real–Time Optical Characterization of Surface Acoustic Modes of Polymide Thin Film Coatings"pp. 1–50, (Preprint) Published Oct. 11, 1992, Journal of Applied Physics No. 72 pp. 2823–2839.

(List continued on next page.)

Primary Examiner—K. Hantis
Attorney, Agent, or Firm—Fish & Richardson, P.C.

[57] ABSTRACT

Samples such as thin polymeric films are analyzed using optically induced phonons by excitation of the sample using radiation preferably absorbed by the sample and probe radiation, preferably not absorbed by the sample, that is diffracted from the surface of the sample. The pulse width of the probe is preferably on the order of the detectable diffraction signal so that the phonon decay from each excitation pulse can be detected and analyzed. The technique is applicable to various samples by inducing a ripple morphology on the sample surface and detection of light diffracted substantially from surface ripple.

58 Claims, 24 Drawing Sheets

OTHER PUBLICATIONS

Duggal et al., "Real–time Characterization of Acoustic Modes of Polymide Thin–Film Coatings Using Impulsive Stimulated Thermal Scattering", Applied Physics Letters, vol. 60, No. 6, Feb. 10, 1992, pp. 692–694.

Burzynski et al., "Study of Anisotropy of Acoustic Wave Propagation in Stretched Poly (vinylidene difluoride Film Using the Picosecond Transient Grating Technique", *Polymer*, vol. 30, Jul. 1989, p. 1247.

Epinet, "Laser–Induced Gratings in Nematic/Cholesteric Mixtures", *Appl. Phys. Lett.*, vol. 50, 26, 29, Jun. 1987, p. 1925.

Whitman et al, Appl. Optics 8, 1567 (1969) No Month Available.

Nizzoli et al., Dynamical Properties of Solids, (ed. G. K. Horton et al, North–Holland, Amsterdam, 1990), vol. 6, 283 No Month Available.

Bortolani et al., J. Phys. C., 16, 1757 (1983) No Month Available.

Fishman, I.M. et al., "Surface selectivity in four–wave mixing: transient gratings as a theoretical and experimental example", J. Opt. Soc. Am. B., vol. 8, No. 9, Sep. 1991, pp. 1880–1888.

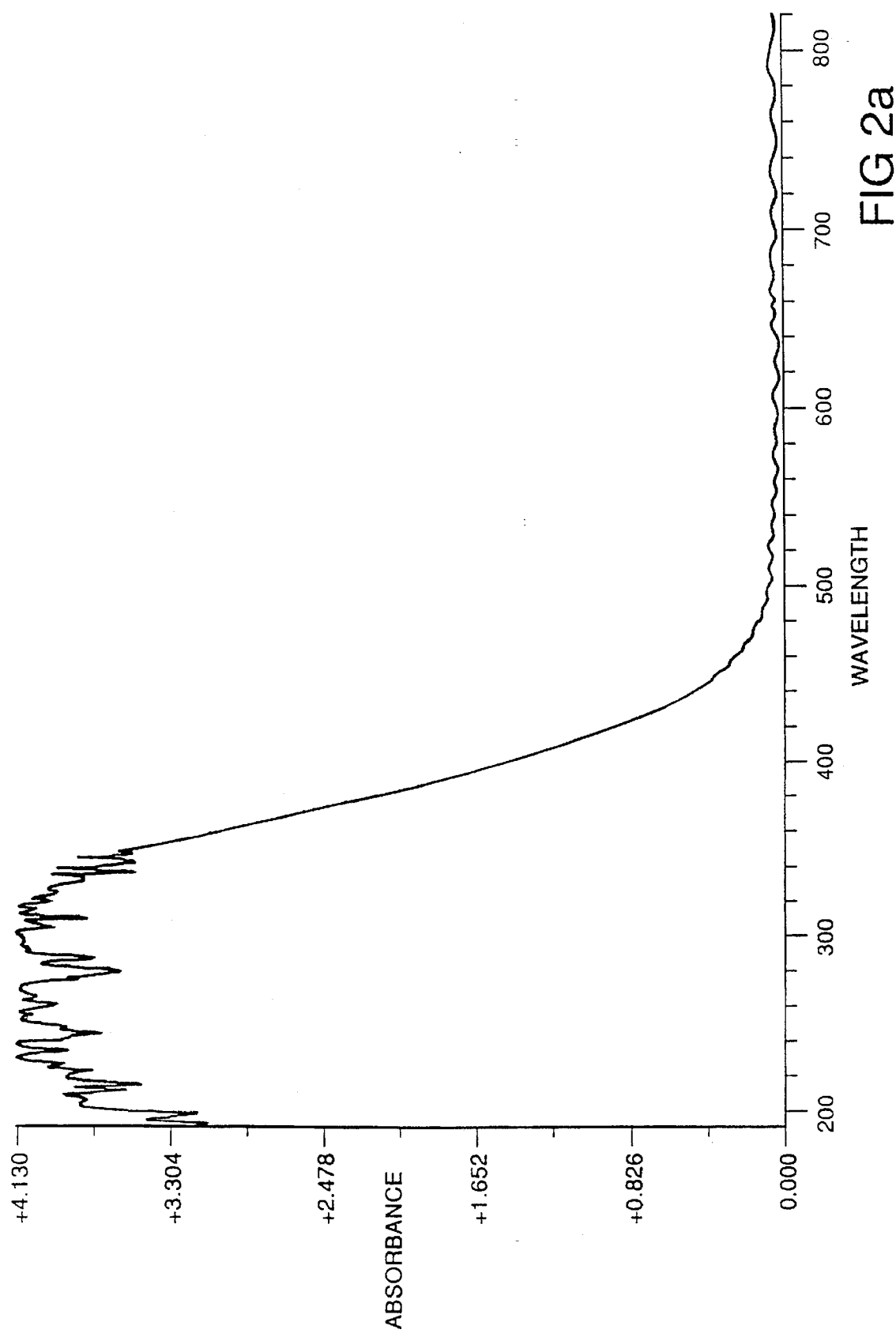

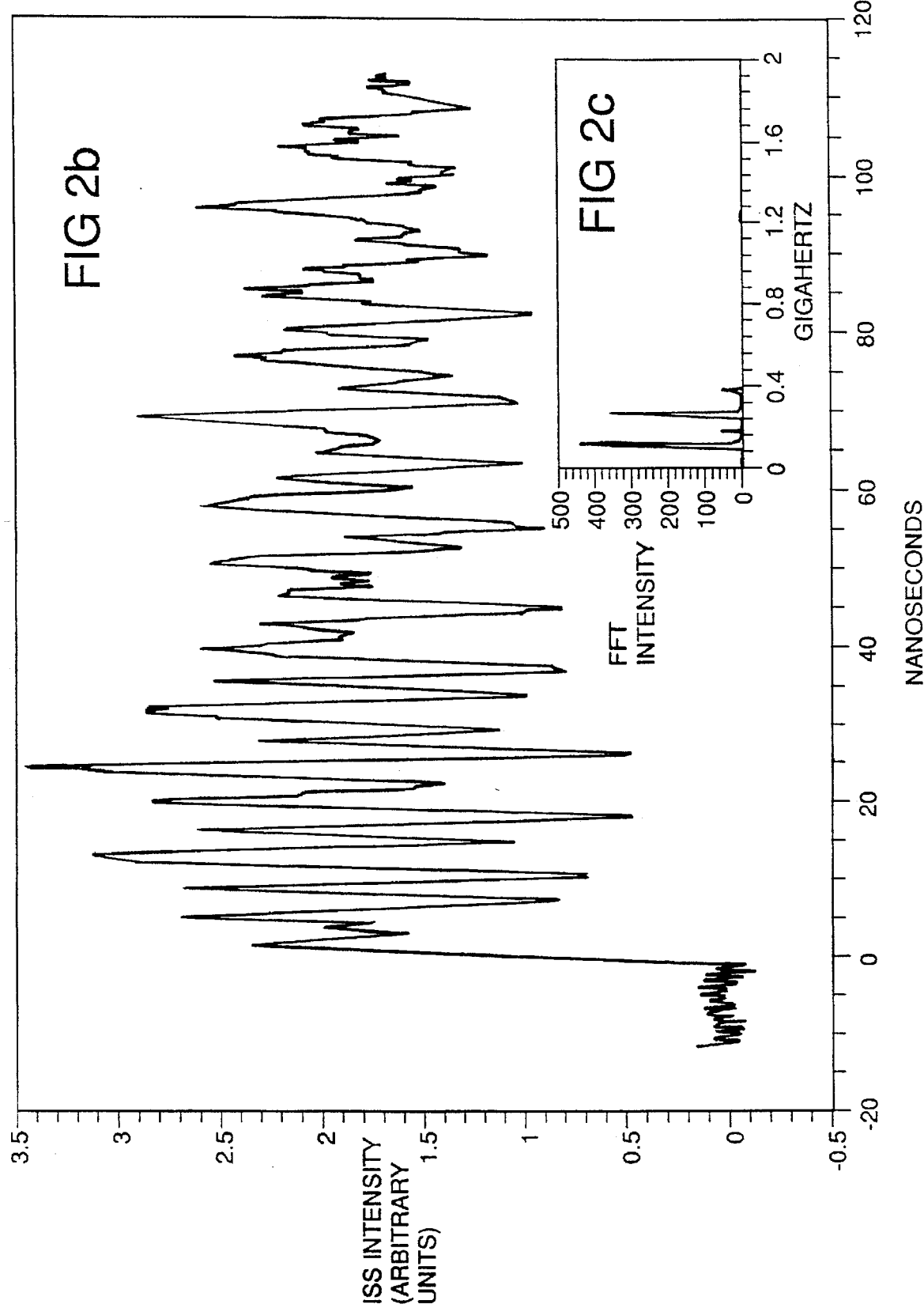

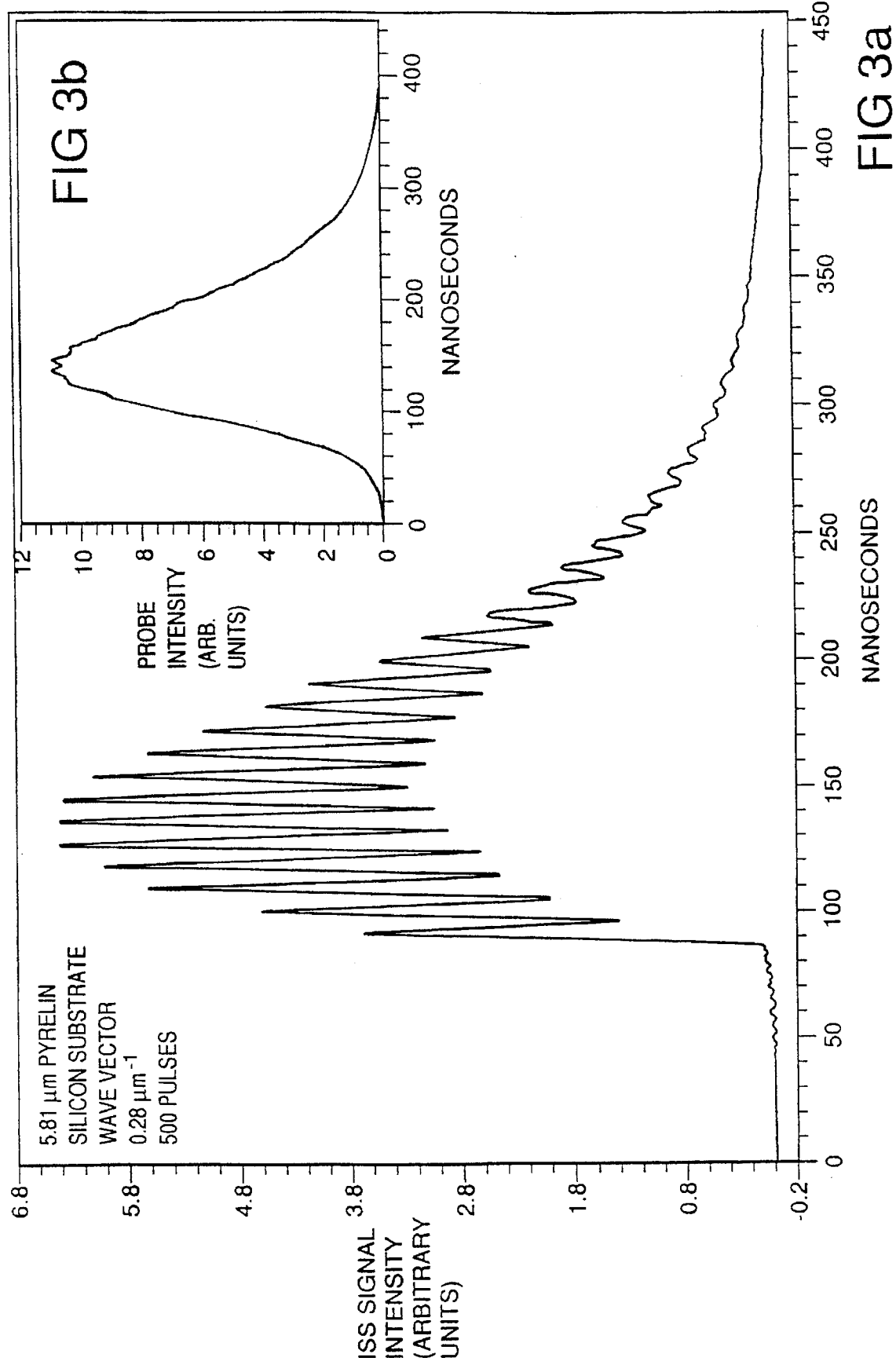

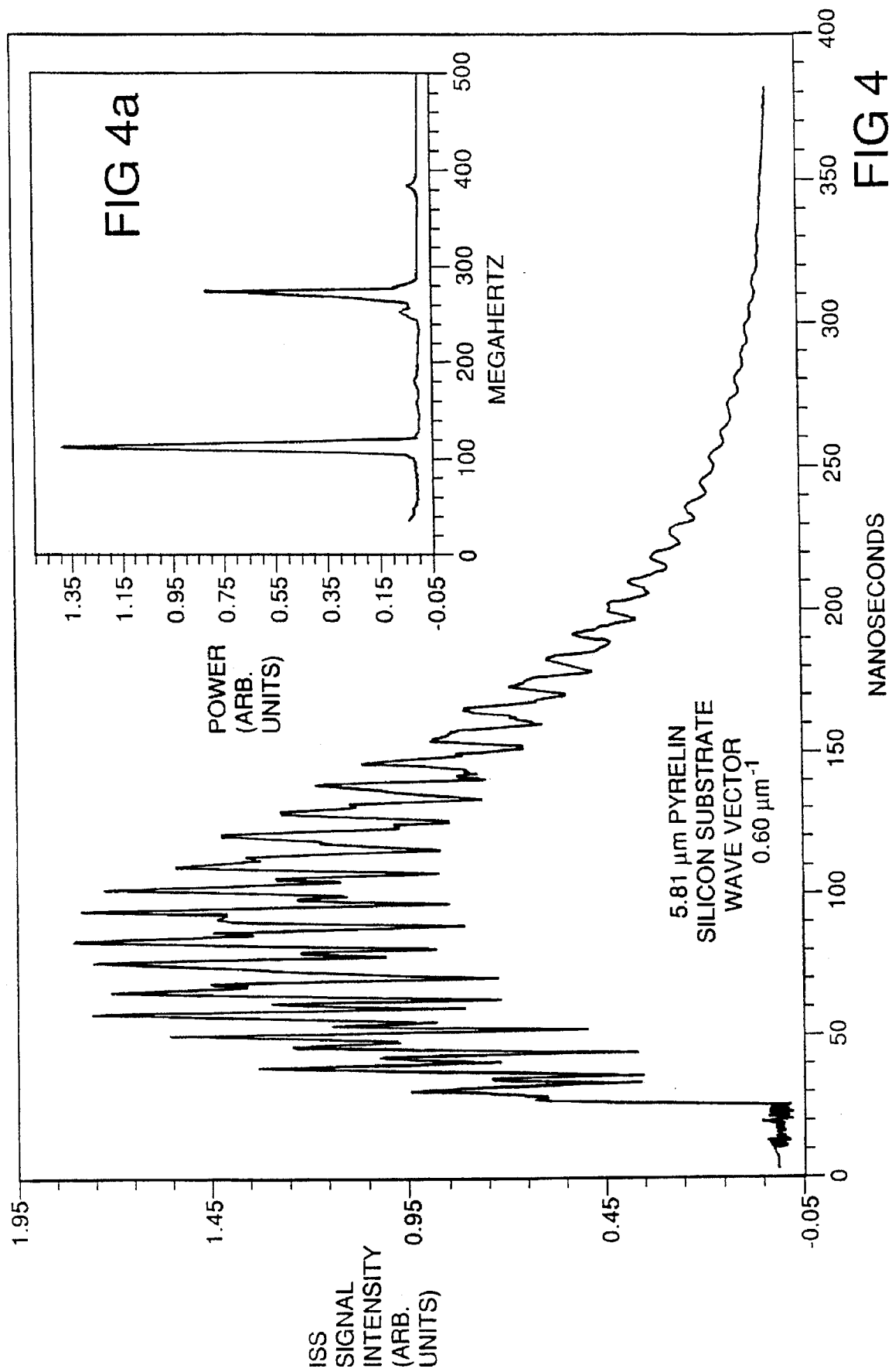

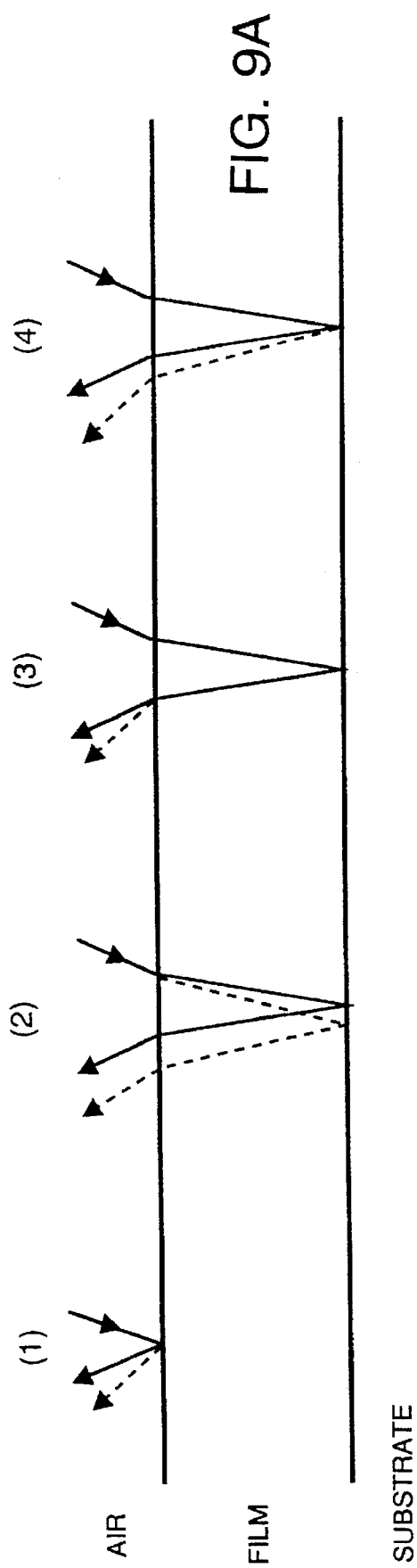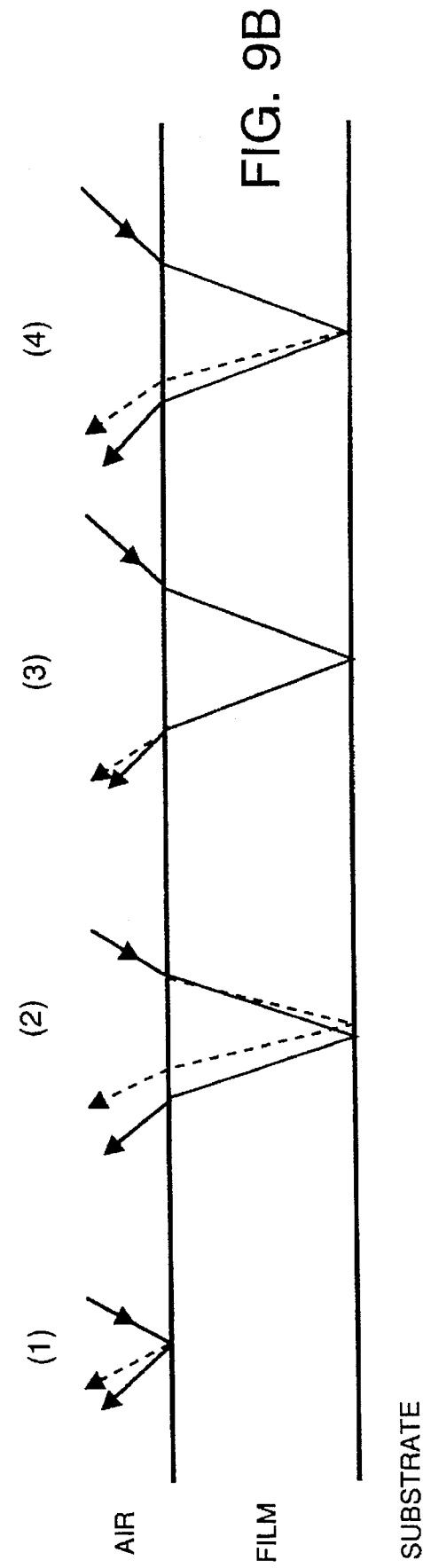

MEASUREMENT OF MATERIAL PROPERTIES WITH OPTICALLY INDUCED PHONONS

This invention was made with government support under contract Number F19628-90-K-0021 awarded by the Air Force. The government has certain rights in the invention.

Cross-Reference to Related Applications

This is a continuation of application Ser. No. 07/910,762, filed Jul. 8, 1992, now abandoned. Which is a continuation-in-part of U.S. Ser. No. 07/726,759, filed Jul. 8, 1991.

FIELD OF THE INVENTION

This invention relates to the measurement of material properties using optically induced phonons.

BACKGROUND OF THE INVENTION

Laser Induced Phonons (LIPS) are produced by time-coincident laser pulses intersecting inside a sample, setting up an optical interference pattern, i.e., alternating intensity peaks and nulls. Energy deposited into the system via optical absorption or stimulated Brillouin scattering results in the launching of counterpropagating ultrasonic waves (phonons) whose wavelength and orientation match the interference pattern geometry. The mechanism by which LIPS ultrasonic waves are generated depends upon whether the sample is optically absorbing or transparent at the excitation wavelength. If the excitation pulses are absorbed e.g. into high-lying vibronic levels, rapid radiationless relaxation and local heating at the interference maxima (the transient grating peaks) occurs. Thermal expansion then drives material in phase away from the grating peaks and toward the grating nulls, setting up counterpropagating waves.

In samples which are transparent at the excitation wavelength, optical energy is coupled directly into the sample's acoustic field via stimulated Brillouin scattering. This process takes advantage of the inherent spectral line width in 100-picosecond (psec) excitation pulses. Higher-frequency photons from each pulse are annihilated to create lower-frequency photons in the opposite pulse and phonons of the difference frequency and wave vector in the medium. Counterpropagating waves (a standing wave) are thus produced.

In either case the acoustic wave propagation, which continues after the excitation pulses leave the sample, causes time-dependent, spatially periodic variations in the material density, and since the sample's optical properties (real and imaginary parts of the index of refraction) are density-dependent, the irradiated region of the sample acts as a Bragg diffraction grating. This propagation of the optically excited ultrasonic waves can be optically monitored by time-dependent Bragg diffraction of a variably delayed probe laser pulse.

SUMMARY OF THE INVENTION

An object of the invention is to make LIPS (alternatively referred to herein as Impulsive Stimulated Thermal Scattering or ISTS) measurements by reflectance of a probe beam from the sample surface without regard to the absorbance of the probe beam by the sample. Another object is to make LIPS measurements without regard to sample type or thickness. A particular object is the analysis of thin, polymer samples by LIPS-reflectance with a non-absorbing probe laser.

The phenomenon which allows realization of these objects is believed to be the inducement of a physical surface morphology or 'ripple' in response to laser excitation. It has been discovered that the surface ripple phenomenon can be selectively induced based on the nature of the sample, e.g. sample stiffness and thickness and the angle of incidence and wavelengths of the excitation radiation and selectively detected or analyzed by control or monitoring of parameters such as angle of incidence, polarization and intensity of a probe beam reflected from the ripple morphology. The discovery enables advantages in terms of the samples that can be analyzed, including ultrathin polymer films, in terms of the rate at which data can be obtained, such as obtaining the full transient signal induced by each excitation laser shot, and in terms of the type and accuracy of data that can be obtained, including more accurate subtraction of probe pulse contribution from the signal and the collection of new data such as acoustic dampings rates (attenuation), thermal conductivity and film delamination.

In a particular example, excitation of a sample using optically absorbing wavelengths can be used to induce the physical morphology, preferably in the form of a periodic grating on the surface of a sample. The grating morphology can be interrogated by reflectance of a probe laser from the surface without regard to the probe laser wavelength and in particular, allowing the use of a probe laser not substantially absorbed by the sample. The sample may be of various types. A particular example is the analysis of thin polymer films. The films, which may be UV-absorbing and visible-transmitting, may be excited by UV pulses and interrogated by reflectance with visible pulses. For very thin samples, e.g., 500, 30, 10 or even 1 µm or less, this operational mode is particularly advantageous since, with a non-absorbing probe laser, sample heating which can easily damage thin samples, is reduced. It is also an advantage that samples can be interchanged without the need for selecting new probe laser wavelengths. Alternatively, in the case of thin samples, e.g., polymer films, acoustic waves may also be excited through impulsive Brillouin scattering in which case the excitation pulses need not be absorbed by the sample.

Another object is to make measurements quickly, with fewer laser shots, to make it possible to observe changing sample properties with high time resolution. Employing techniques of the invention, LIPS measurements may be made in real time. An excitation pulse having a short pulse width compared with the phonon oscillation period may be employed in combination with a high power probe laser having a relatively long pulse width such that a substantial time-portion, in many cases all, of a sample's transient time dependent response from each excitation pulse can be measured. While a high power probe may be particularly useful in some circumstances, alternatively, it has been discovered that signal can be obtained using a relatively low power probe, e.g. about 1 watt, provided by a CW source such as an argon ion laser. In either case, the probe signal from successive excitation pulses may be signal averaged to increase signal to noise. The detection electronics are selected so they have sufficiently fast response times to permit time resolution of the phonon oscillations. Operation in these modes is, again, particularly advantageous for thin, polymer samples since the number of excitation pulses can be reduced and thus the number of heating cycles, which can potentially damage thin, fragile samples can also be reduced. For a probe which has a short width compared to the lifetime of the transient response, a temporal delay between excitation and probe pulses may be varied to interrogate the sample at different time segment stages in its response evolution.

The term "polymers" as used herein refers to molecules composed of sequences of repeating monomer units connected by covalent bonds. A particular polymer is generally not made up of a single molecular species. Rather, polymers are mixtures of macromolecules with similar structures and molecular weights that exhibit some average characteristic properties. The polymers may be homopolymers or copolymers, linear or branched, cross-linked or bonded by electrostatic interaction such as hydrogen bonds. The polymers may be elastomers, thermoplastics and may include plasticizers, stabilizers, anti-oxidants and lubricants. Polymers may be crystalline in the sense that long segments of linear polymer chains are oriented in a regular manner with respect to one another. Such crystalline regions of a polymer are referred to as crystallites. Amorphous, noncrystalline regions generally lie between the crystallites and constitute defects in the crystalline structure.

A "sample" such as of a polymer may include additives, e.g., chromophores incorporated within the polymer mass (typically not covalently bonded) for enhancing absorbance of the sample at a particular wavelength such as a desired excitation or probe wavelength. A "pure sample" as used herein contains no such additive.

The term "absorption", as used herein, includes absorption of electromagnetic radiation by ground or excited states of the sample molecule. Particular aspects of the invention use LIPS in the reflectance mode where the absorbance of the probe is less than the absorbance of the excitation. Particularly the probe absorbance is 50%, 10% or even 1% or less than the excitation absorbance. In some cases, no absorbance of the probe beam by the sample can be detected. Molar absorptivities (E) at the probe wavelength may be less than 1000 or 100. Absorption may be less than about 10% of the maximum absorption (which may be relative to complete absorbance) in a wavelength region (e.g., UV, visible, infrared), typically less than 1%. The excitation wavelength is selected such that the absorbance is sufficient to give rise to a periodic morphology on the sample surface, detectable as a diffraction signal.

In a particular aspect, the invention features an apparatus for measuring the properties of a sample of material. The apparatus includes a first, excitation source for producing excitation radiation adapted to impinge upon the sample of material. The excitation radiation is comprised of pulsed radiation composed of at least two component pulses which interfere within the sample. The excitation radiation is sufficient to induce a transient phonon in the material which gives rise to a transient, time dependent periodic ripple morphology on a surface of the sample. A second, probe source is provided for producing probe radiation arranged to reflect from the periodic ripple morphology on the surface of the sample to form a diffraction signal. A detector detects the diffraction signal from the probe source radiation reflected from the surface, and an analyzer selectively analyzes the diffraction signal formed by the transient ripple morphology.

In another particular aspect, the invention features a method for measuring the properties of a sample. The method includes impinging a pulse of excitation radiation upon the sample. The excitation radiation is composed of at least two component pulses which interfere within the sample and are selected to induce a transient phonon in the sample which gives rise to a transient, time dependent ripple morphology on a surface of the sample. Probe radiation is reflected from the periodic ripple morphology on the surface of the sample to form a diffraction signal. The diffraction signal from the probe source radiation reflected from the ripple morphology is selectively detected.

In another particular aspect, the invention features an apparatus for measuring the properties of a thin sample of polymeric material. The apparatus includes a first, excitation laser source for producing a pulse of radiation adapted to impinge upon the sample. The excitation source is a pulsed source composed of at least two component pulses which interfere within the thin film. The excitation radiation is adapted to induce a transient phonon in the material. A second, probe laser source is provided for producing radiation. The probe radiation is of selected wavelength not substantially absorbed by the sample and arranged to reflect from the surface of the sample to form a diffraction signal. A detector detects the diffraction signal.

The features of the above aspects can be combined. Apparatus features can be used in method inventions. In addition, in various aspects the invention may include one or more of the following features. The radiation from the probe source is absorbed about 50%, 10% or 1% or less than the radiation from the excitation source or there is no detectable or substantial absorbance by the sample at the probe wavelength. The excitation source of radiation is in the ultraviolet. The probe source is in the visible. The sample is a thin sample, e.g., on the order of about 500, 30 or 10 µm or less, and the excitation radiation is absorbed by the sample. The sample is a thin polymeric film. The film is a free-standing film or disposed on a support. The probe radiation is diffracted from the surface of the sample. The probe beam and detector are for detecting a substantial time-portion of the time-dependent diffraction signal, induced by each excitation pulse such as the entire detectable time-dependent diffraction induced by each excitation pulse. The probe radiation is of a selected pulse width and the detector is adapted to detect the time dependent diffraction for the duration of the probe pulse. The excitation pulse width is on the order of psec duration and the probe pulse width is on the order of nanosecond (nsec) duration (e.g. generally greater than 10 nsec, e.g. around 100 ns). The detector has a time resolution on the order of 1 nsec. A signal averaging means is provided for signal averaging the diffracted radiation from multiple excitation pulses. The probe pulse has a peak power output (power during the laser on-time) of about 1000 watts or greater, such as around 10,000 watts. The probe laser is a Q-switched YAG laser. The excitation pulse is generated from a pulsed laser and the probe pulse can be generated from a CW laser having for example a laser power output of around 1 watt, such as a gated argon ion laser. The polymer sample is a pure polymer sample.

Various aspects may also include one or more of the following features. The diffraction signal is analyzed to selectively analyze diffraction from surface ripple. The analyzer includes a polarizer for determining change of polarization of the probe beam after diffraction to selectively analyze diffraction from the surface morphology. The analyzer may also be for analyzing the signal as a function of wavevector to selectively analyze diffraction signal from the ripple morphology. The angle of incidence of the probe beam and/or the excitation beam or the wavelength of the excitation beam may be varied to optimize diffraction from the ripple morphology. The diffraction signal is produced by reflection of the probe beam from the back surface of a sample, opposite the radiation sources or the front surface or both. The system is adapted for determining adhesion and/or thermal diffusion of the polymer sample on a substrate surface from the diffraction signal.

The invention has many advantages and applications. It is demonstrated below that ISTS experiments with real-time data acquisition rates are possible and can be applied to studying the pseudo-Rayleigh acoustic modes that propagate in thin film coatings. Real-time data acquisition can be crucial in avoiding optical damage to polymer films. The diffracted ISTS signal arises predominantly from corrugation or ripple displacements at the film surface and the film/substrate ripple due to the propagating pseudo-Rayleigh modes. The relative contribution of each acoustic mode to the ISTS signal depends on the efficiency with which each mode is excited by the excitation pulses and on the efficiency with which each mode diffracts the probe beam due to surface and interface ripple. A formalism is developed to quantify both of these factors. Using this formalism a method for extracting the elastic constants of the film by analyzing the dispersion of the pseudo-Rayleigh modes is described and applied to the polyimide/silicon system.

The techniques have wide applications in nondestructive, real-time characterization of thin films. For many applications, such as monitoring thin-film fabrication and cure or determination of the spatial uniformity of coatings, it is not necessary to determine elastic moduli but merely to monitor changes in acoustic frequency. Finally, characterization of thermal diffusion rates will present a similar range of applications in polymeric, diamond, and other thin films. Other types of materials can be studied, for example, single crystal Fe films and amorphous, plasma deposited carbon films.

The invention includes methods of use of the techniques described. Still other objects, features and advantages follow.

DETAILED DESCRIPTION

We first briefly describe the drawings.

Drawings FIGS. 1 to 1c illustrate schematically, the surface ripple morphology phenomenon included in the present invention;

FIG. 2 is a schematic of a measurement apparatus according to the invention; FIG. 2a is an absorbance spectrum of a polymeric sample; FIG. 2b is a plot of the intensity verses time, raw data, from the experimental setup in FIG. 2; and FIG. 2c is a plot of the processed data;

FIG. 3 is a schematic of an alternative measurement apparatus according to the invention; FIG. 3a is a plot of the intensity verses time, raw data, from the experimental setup in FIG. 3; FIG. 3b is a plot of the probe pulse intensity; FIG. 3c is a plot of the processed data from FIG. 3a and FIG. 3d is a plot of processed data taken under the conditions of FIG. 3a, but from a single excitation shot;

FIG. 4 is a plot of intensity versus time raw data, and FIG. 4a is a plot of the processed data from an experimental set up similar to FIG. 3, with an acoustic wavevector of 0.60 $\mu m^{-1}$;

FIG. 5 is a plot of intensity versus time, raw data, from an experimental set up using a CW probe laser while

Figure 8:
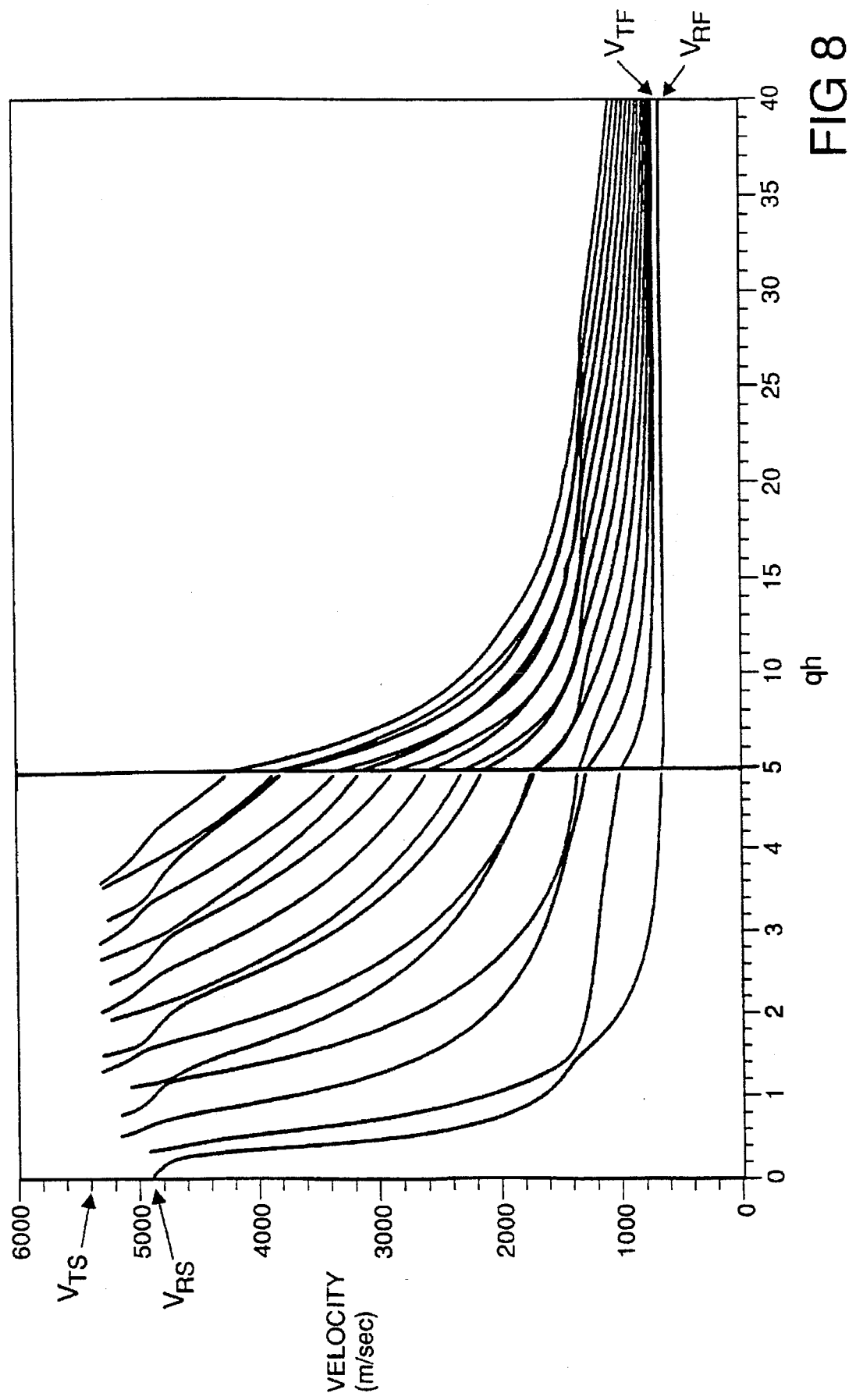
Figure 10:
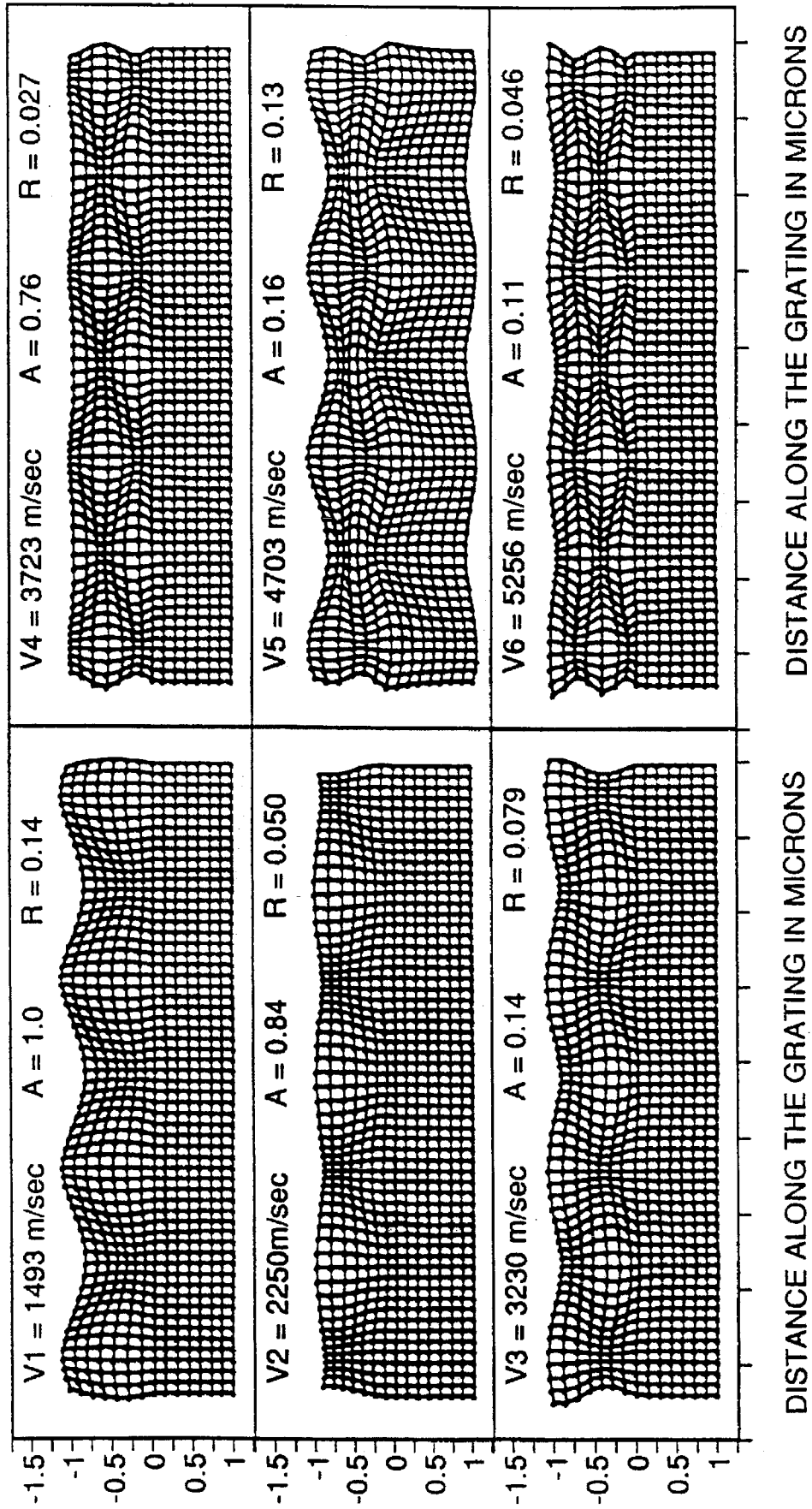
Figure 11:
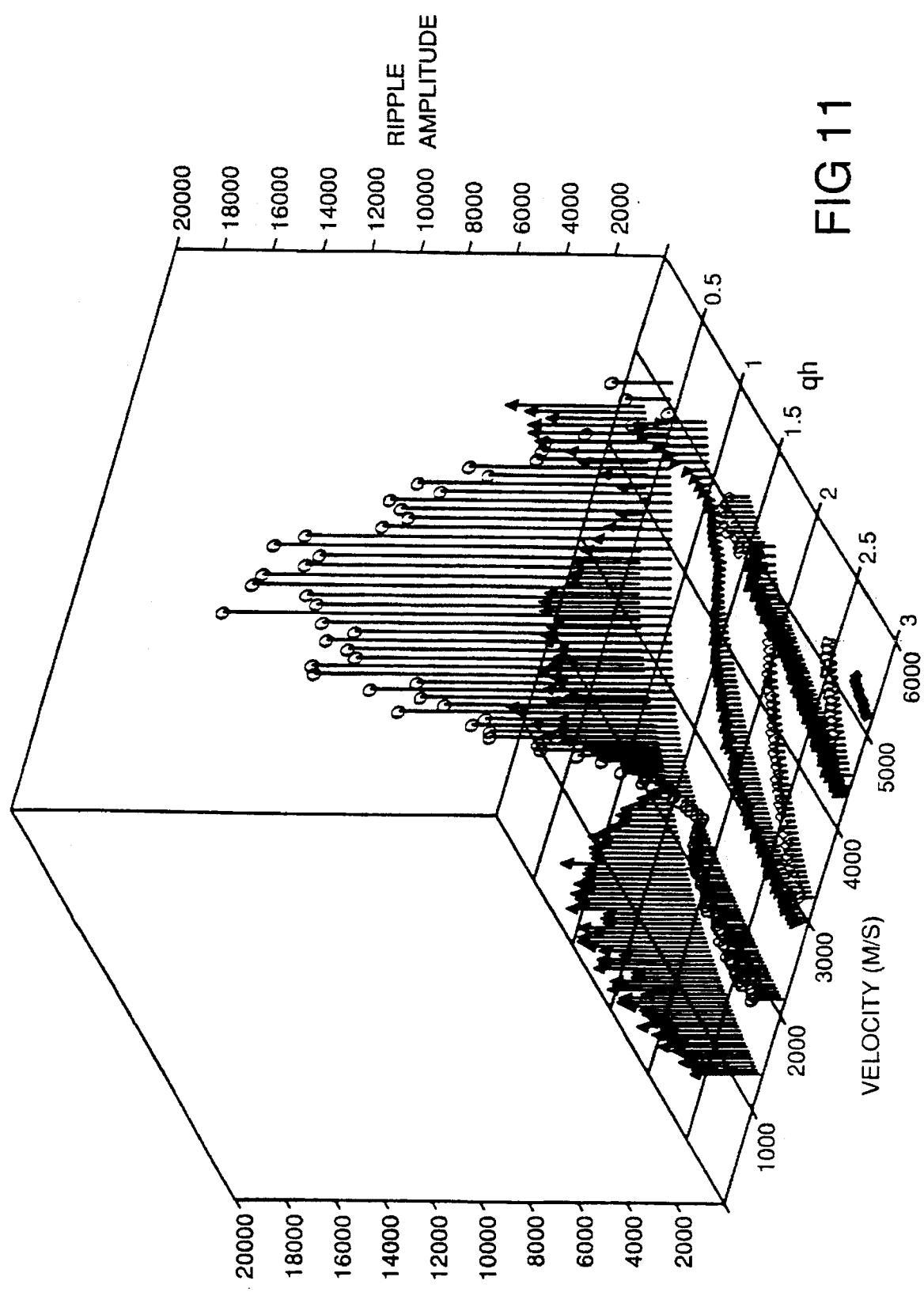
Figure 12:
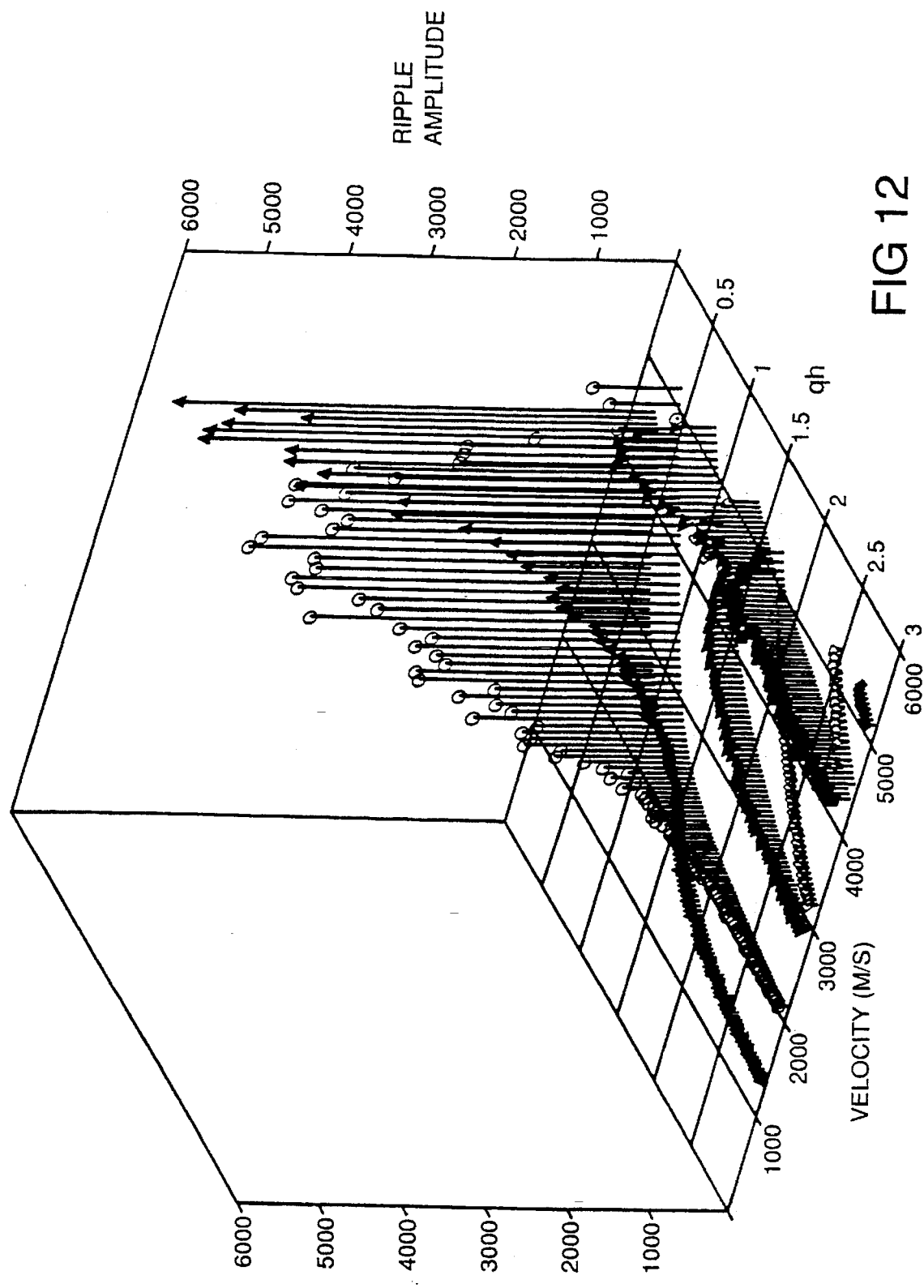
Figure 13:
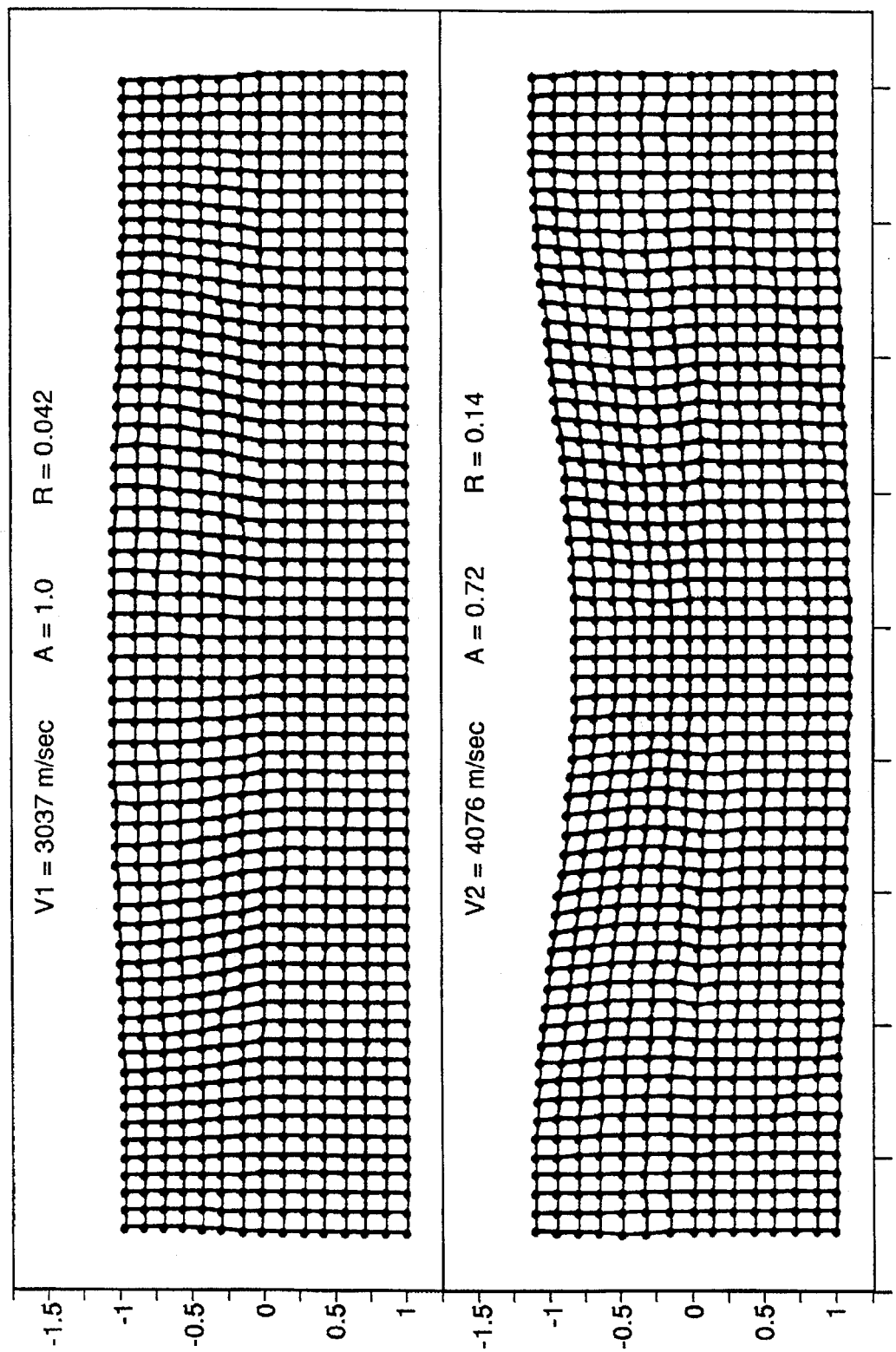
Figure 14:
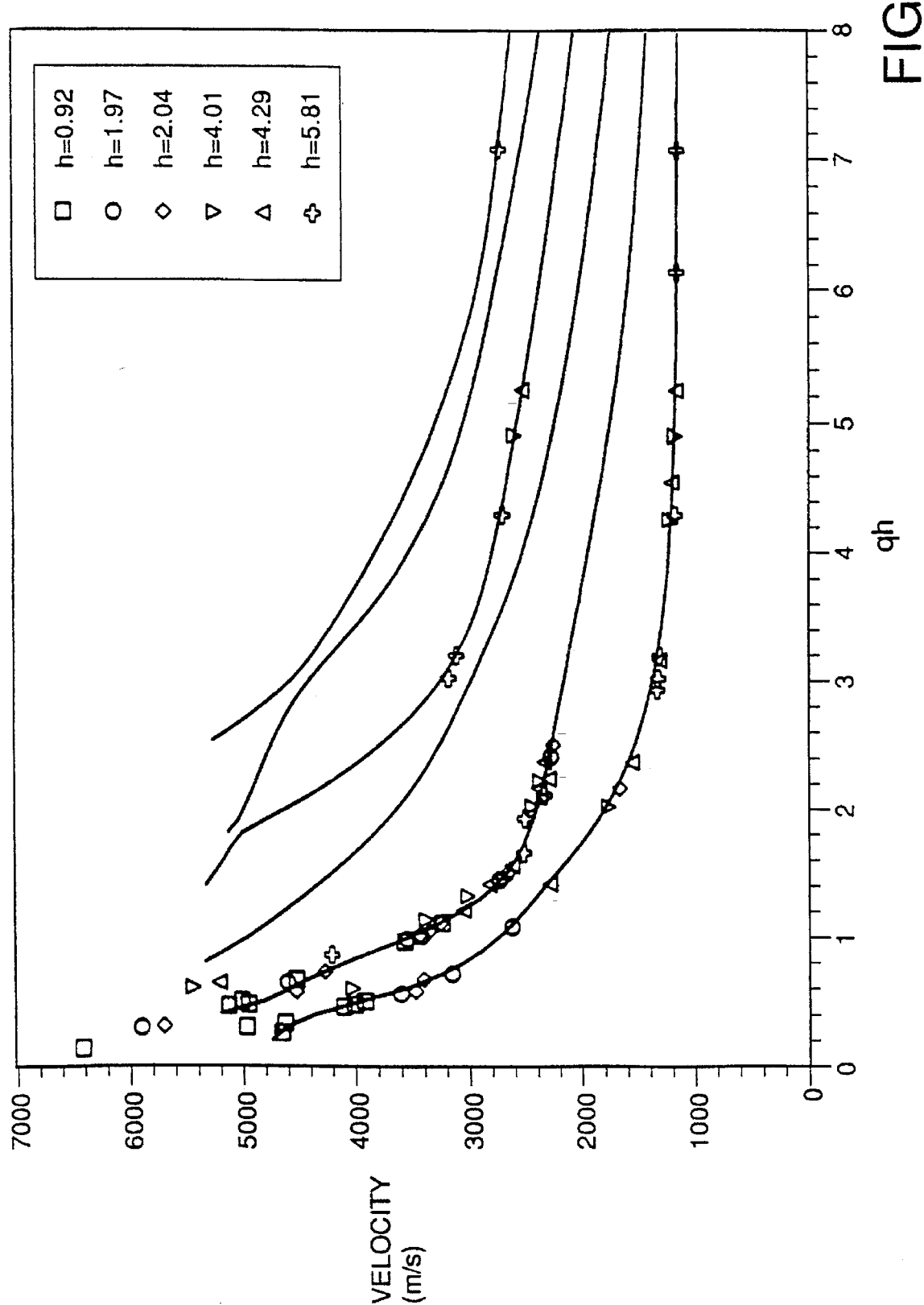
Figure 15:
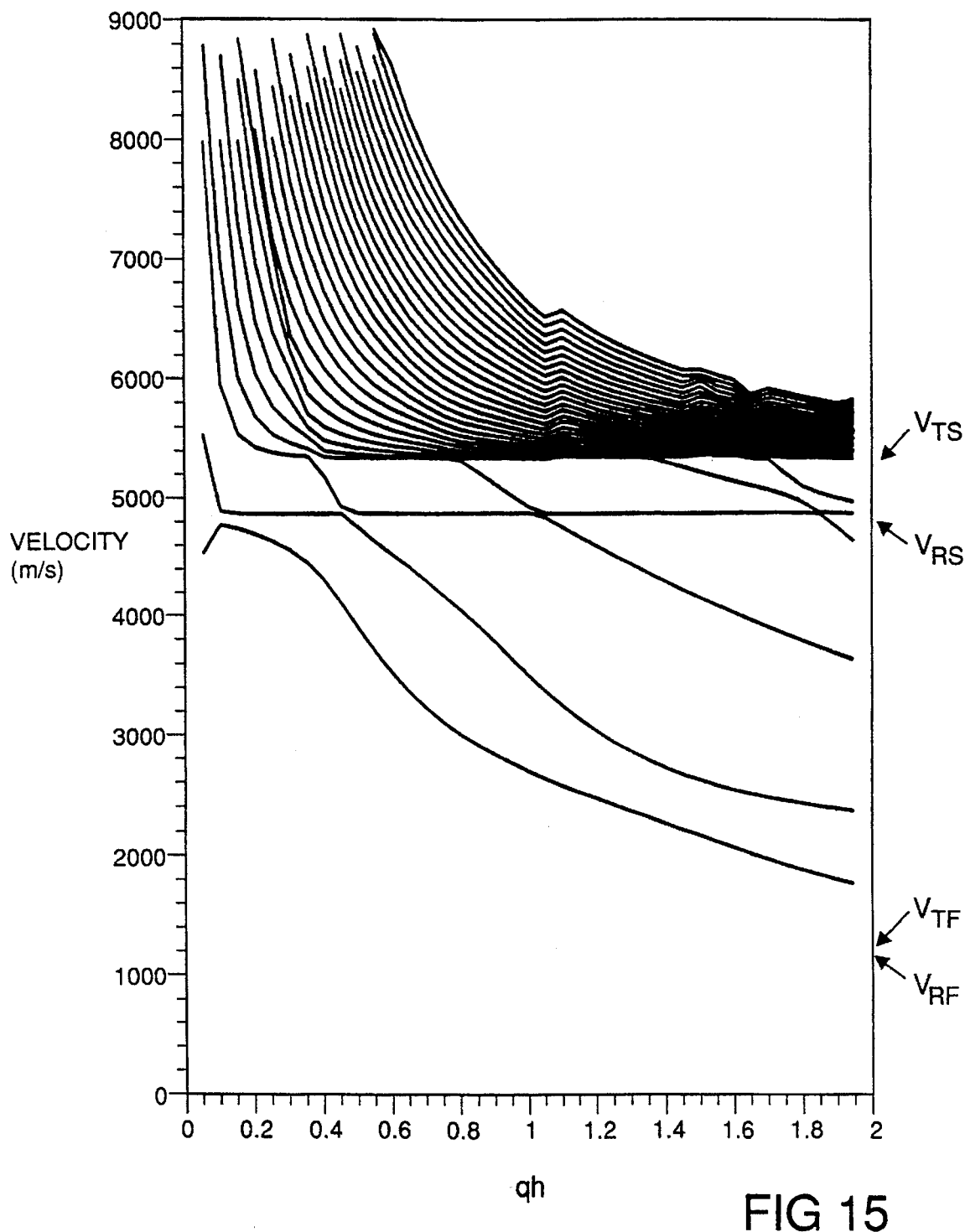
Figure 16:
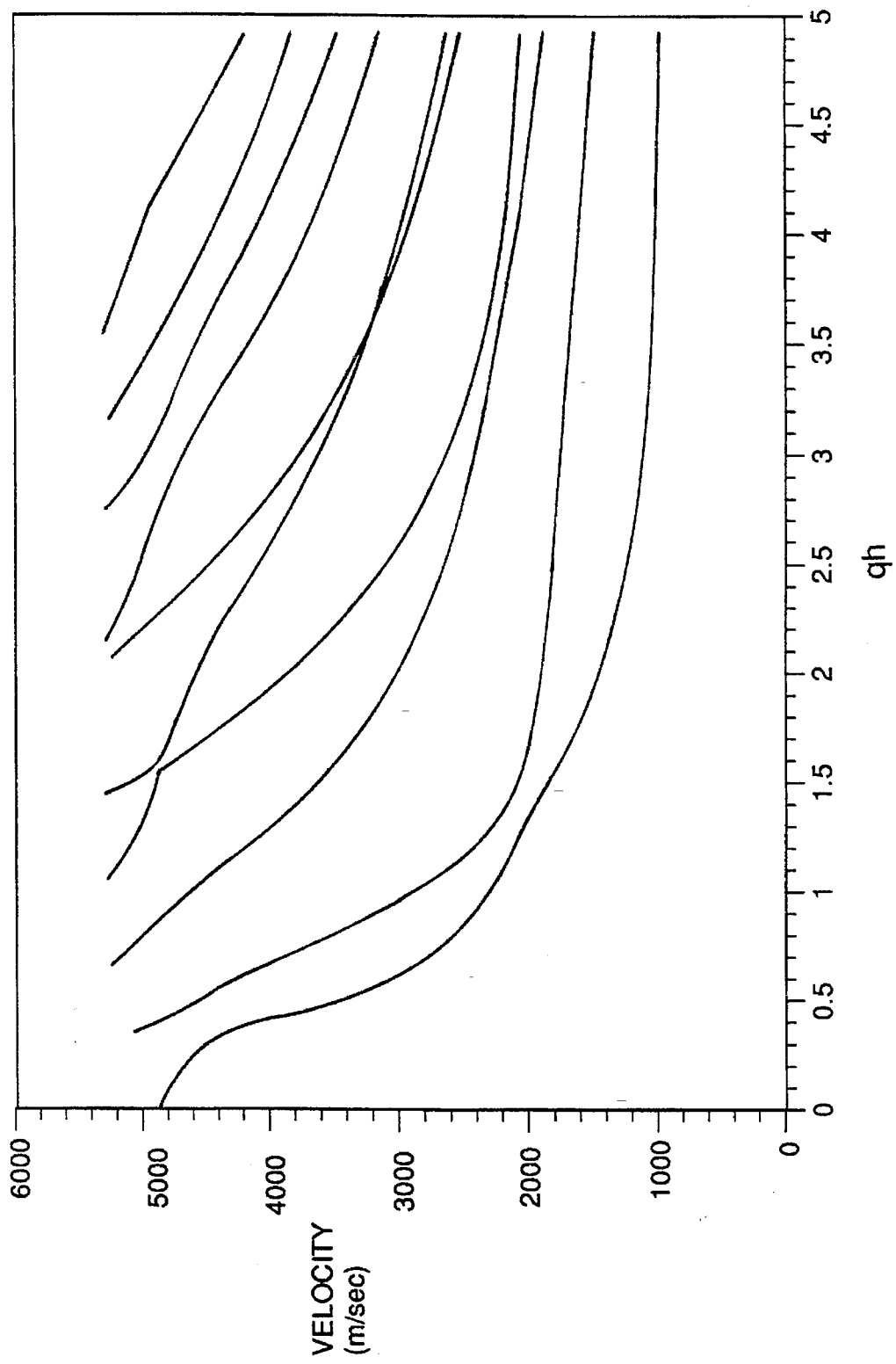
Figure 16A:
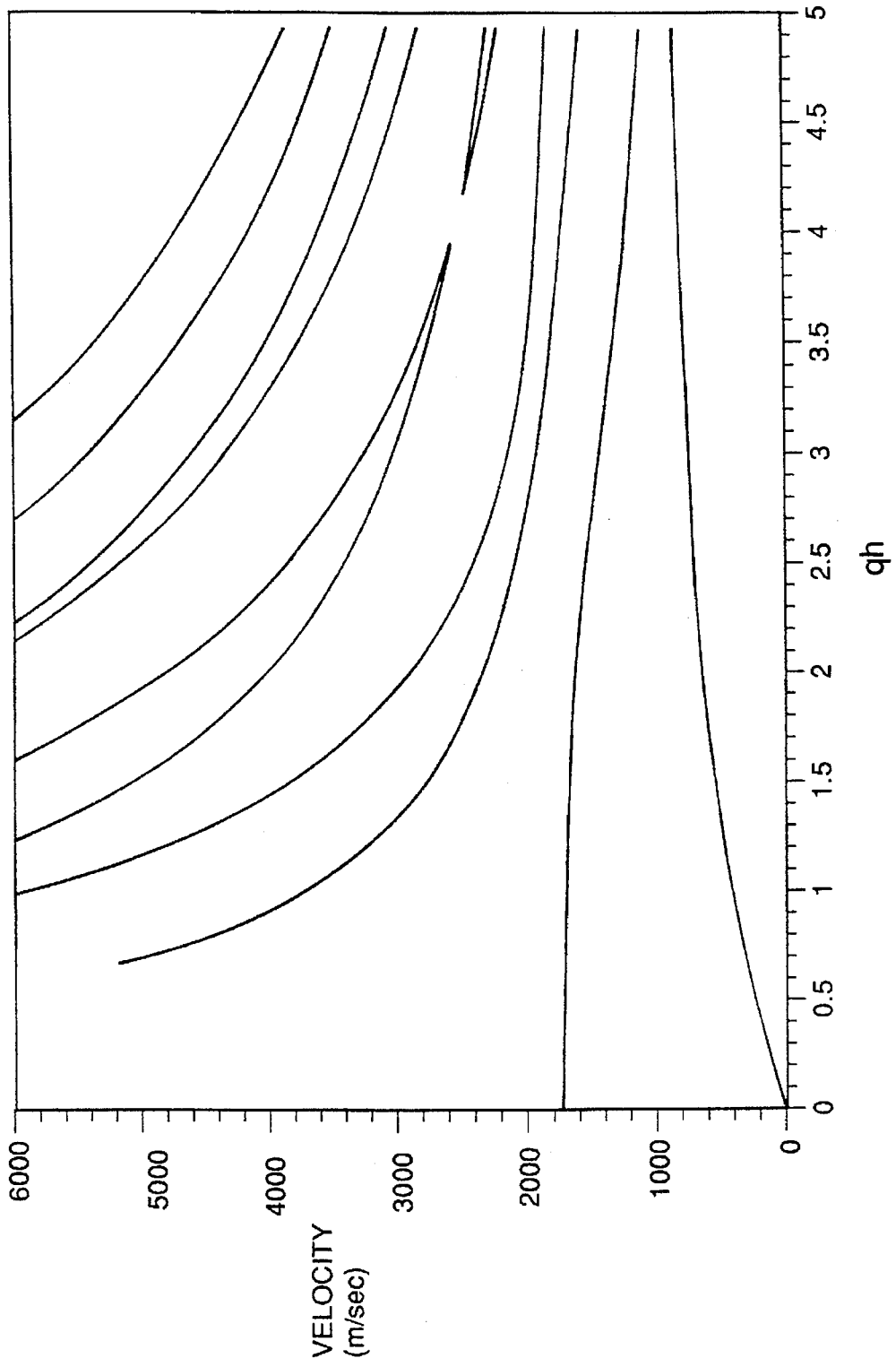
Figure 17:
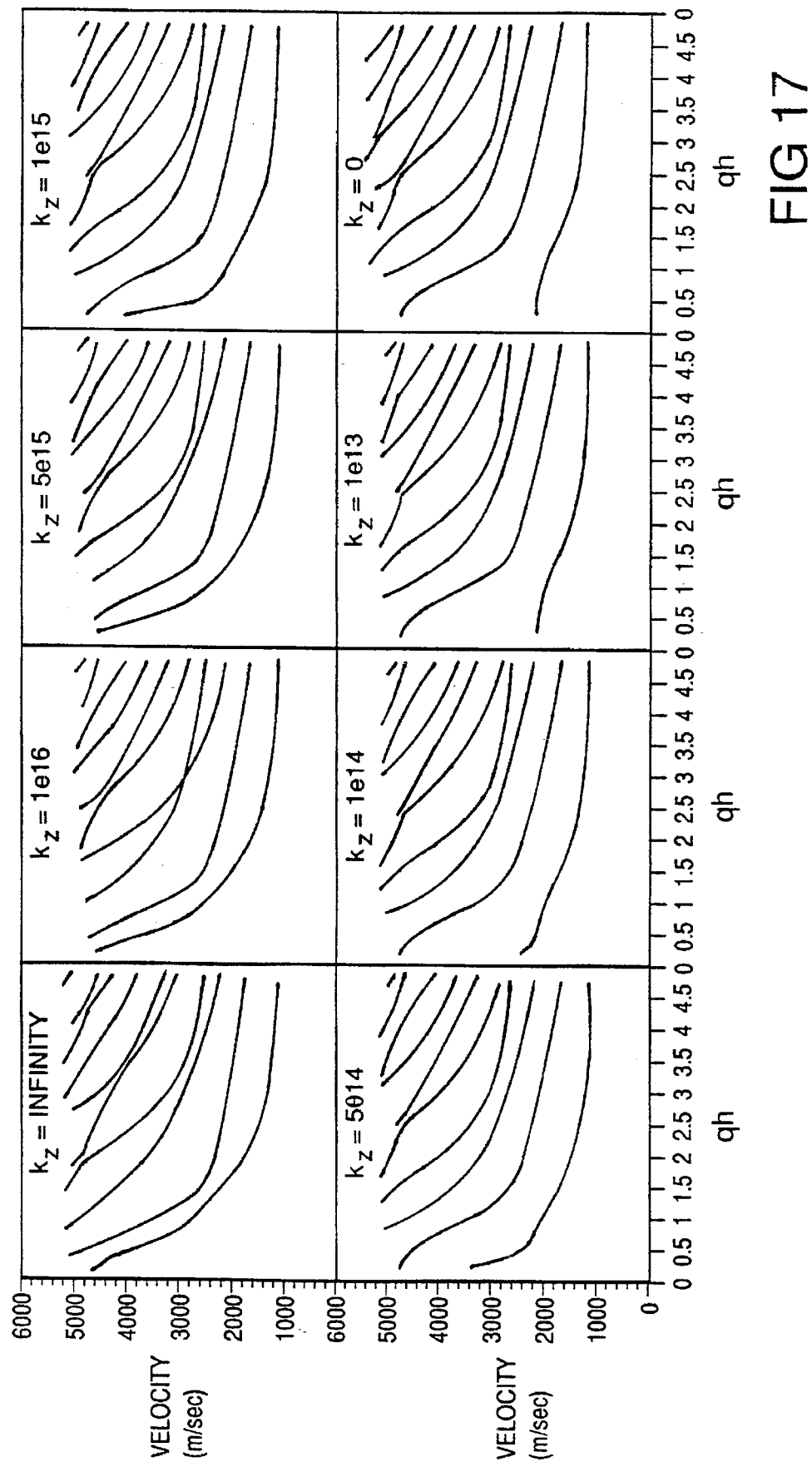
Figure 18:
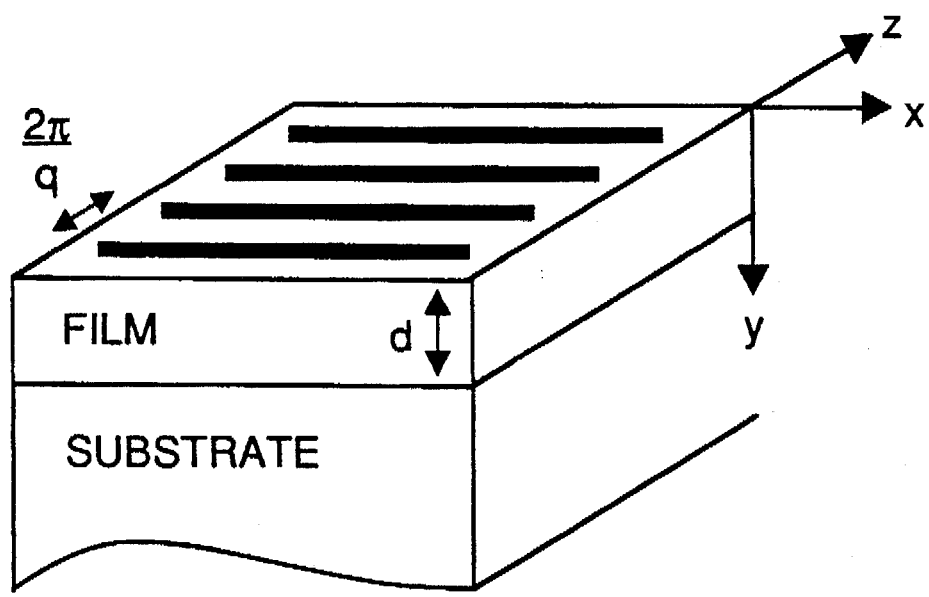

FIG. 8 is a plot of pseudo-Rayleigh mode dispersion generated using substrate elastic parameters $V_{Ls}$=8945 m/s, $V_{Ts}$=5341 m/s, $\rho_s$=2.33 g/cm$^3$ and film elastic parameters $V_{Lf}$=1300 m/s, $V_{Tf}$=700 m/s, $\rho_f$=1.45 g/cm$^3$, with the acoustic wavevector given by q, the film thickness is h, and $V_{Rs}$ and $V_{Rf}$ are the substrate and film Rayleigh surface velocities respectively;

FIG. 9 is a schematic illustration of the beam paths for the four components of first order ripple diffraction that contribute to ISTS signal, wherein parts A and B describe the different paths for the two orders of diffraction observed experimentally;

FIG. 10 illustrates material displacements, generated using the optimized (for the system studied) elastic constants, for the first eight pseudo-Rayleigh modes on a 1 μm film coating an infinite substrate at a qh value of 2.5, with the scale factors (A) for each mode determined such that the largest component of displacement in the mode which is driven most efficiently is equal to one and the ripple amplitude (R) for each mode given relative to the maximum displacement amplitude for that mode;

FIG. 11 is a plot of the film surface ripple amplitude versus qh and velocity for a given ISTS heat input using the optimized (for the system studied) elastic constants wherein each symbol represents a different mode dispersion curve to facilitate comparison with FIG. 14 and the units of the z axis are arbitrary;

FIG. 12 is a plot of the film-substrate interface ripple amplitude versus qh and velocity using the same parameters as FIG. 11 and the units of the z axis are the same as those given in FIG. 11;

FIG. 13 is a plot of lattice distortion of the first two modes at qh=0.8, which, upon comparison with FIG. 11 indicates the existence of a crossover;

FIG. 14 is experimental data (symbols) and theoretical pseudo-Rayleigh mode dispersion curves (solid lines) for pyralin films on silicon substrates with various film thicknesses (h) in microns; the elastic parameters used in generating the dispersion curves were optimized to best fit the data that fall on the lowest two velocity curves;

FIG. 15 is a plot of dispersion curves for the first 30 normal modes for a 3 μm film on a 330 μm substrate using the optimized elastic constants for the pyralin/silicon system; the existence of modes is illustrated with velocities above $V_{Ts}$ which was the cut-off value for the pseudo-Rayleigh modes calculated for an infinite substrate as in FIGS. (6) and (12);

FIG. 16 is a dispersion curve plot of velocity versus wavevector for a tightly bound film-substrate system, while FIG. 16a is a similar plot for a freestanding film;

FIG. 17 is a series of dispersion curve plots of velocity versus wavevector;

FIG. 18 illustrates the system geometry for an analysis of thermal diffusion.

GENERAL DESCRIPTION

Figure 1:
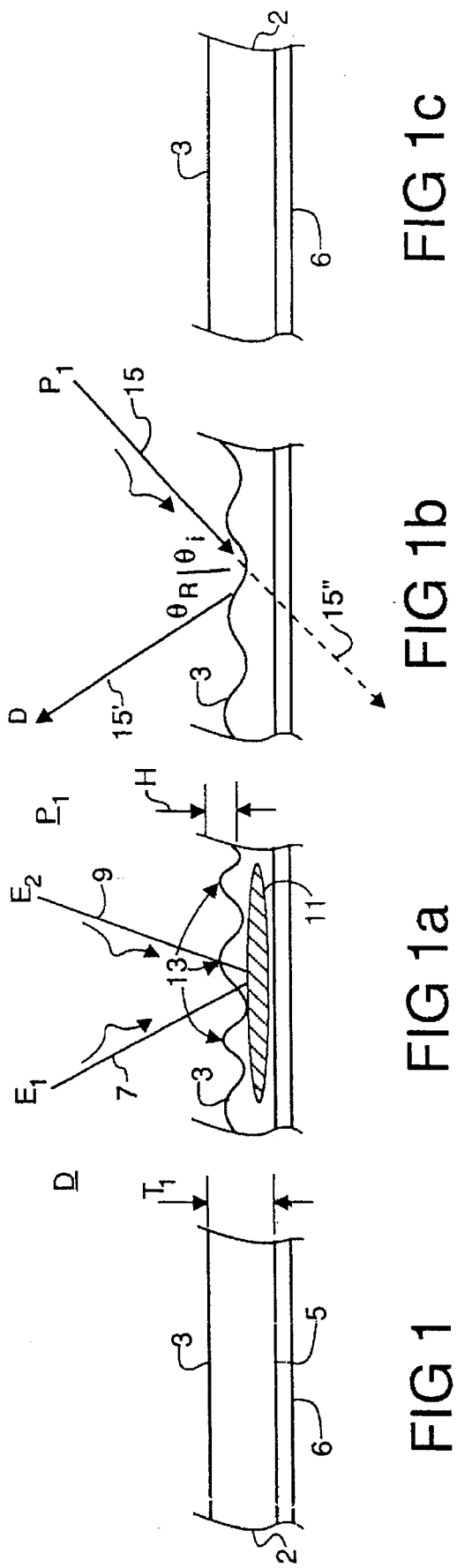

Referring to FIGS. 1–1c, a sample 2, typically a thin $T_1$, e.g. 5 μm thick or less, polymer thin film is provided having a front exposed surface 3 and a back surface 5 which is disposed on a substrate 6. (It will be understood that the film could be, as well, a free standing film, without substrate 6.) As shown in FIG. 1a, the sample is excited by impinging a pair of excitation beams 7,9 from sources $E_1$, $E_2$. The wavelength of radiation from $E_1$ and $E_2$ is selected such that it is absorbed by the sample. The beams 7,9 interfere within an overlap region 11 within the bulk of the sample, causing rapid local heating in a periodic fashion. Upon such excitation, a periodic ripple-like morphology 13 is generated at the surface 3. The morphology has a peak to trough height, H, that is at a maximum soon after absorption of the excitation wavelengths and then oscillates and decays with time. In particular experiments, as discussed below, maximum heights H, are estimated on the order of 5–10 nanometer (nm). As shown in FIG. 1b, the morphology 13 may be interrogated by a probe laser pulse 15, from a source P1, by diffraction of the pulse in the reflection mode from the surface 3. The diffracted beam 15' is detected by a detector D, positioned on the same side of the sample as the source $P_1$. The angle of incidence of the probe, $\theta_i$, and angle of diffraction $\theta_r$, may be varied and selected based on the spacing of the periodic morphology. The source $P_1$ is preferably selected such that the wavelength of the probe pulse is not substantially absorbed by the sample. As illustrated, a component 15" of the beam 15 may be transmitted through the sample. The pulse 15 is typically selected such that its duration is long compared to the excitation pulse and the lifetime of the periodic morphology. The pulse may be from a pulsed probe laser of selected pulse width and energy or a continuous wave laser, for example. The detector is adapted to receive the signal pulse 15', which is the diffracted beam component from the sample surface, for analyzing the characteristics of the morphology over the course of its existence from each excitation. As illustrated in FIG. 1c, after analysis, the sample 2 returns to its original state.

The excitation wavelength is preferably in the ultraviolet (about 100–400 nm), but may be, e.g., in the visible (about 410–800 nm), infrared (about 0.1–50μ) or beyond. The probe is preferably in the visible, but maybe in other regions, e.g. infrared or ultraviolet, depending on sample absorbance. The excitation and probe radiation may be in the same wavelength region. An advantage of the invention is that the sample may be probed with a laser wavelength independent of the sample absorption; greater flexibility is provided in the choice of the probe laser. In particular, it is advantageous to employ a probe laser emitting visible light which can be easily aligned in manufacturing applications. As further discussed in the examples, analysis times can be reduced by employing a probe pulse width as long as the transient decay of the induced phonons, so that the entire morphology decay is detected from each excitation.

A particular advantage is the analysis of thin films, especially thin polymer films, e.g. 10 μm thickness or less, or even 1 μm thickness or less. Typical polymer samples include visible wavelength transmitting polymers such as polyethylene, polyurethane and polyimides. Polymer films which may be analyzed include molecular films such as Langmuir-Blodgett films or biological films. The films analyzed may be supported on a substrate or may be freestanding films. In the case of films on a substrate, the support provides both mechanical rigidity and can reduce sample damage when the support acts as a heat sink. Sample supports include silicon or glass. Applications for the system include analysis of polymer protective coatings on silicon substrates and various applications to polymers in polymer processing, including in-situ processing during e.g. extrusion. In the latter case, the analysis may be carried out at various points in the extruder to determine the progress of the operation and to modify the extrusion in response to the data obtained. Other polymer applications include polymer curing and polymer loading (analysis of properties under mechanical load).

The properties that can be measured by analysis of the raw data include acoustic speeds, determined from the frequency of surface oscillations; attenuation rates determined from decay of the signal; thermal expansion and thermal diffusion rates; thermal expansion coefficients and heat capacities can be determined from signal intensities cases where standard samples are run; compressibility and elastic modulus may be determined from acoustic speed and sample thickness frequency dependencies. Calculation of many properties from the raw data is known in the art, and is further discussed in *Journal of Chemical Physics* 94, 7677 (1991) and Farnell et al., "Elastic Wave Propagation in Thin Layers", *Physical Acoustics*, (W. P. Mason, R. N. Thurston Eds.) 935FF, Academic Press, New York, 1972. A particular method for measuring thermal diffusion is discussed below. Calculation of excitation efficiencies is also discussed below.

EXAMPLE 1

Short probe Pulse

Figure 2:
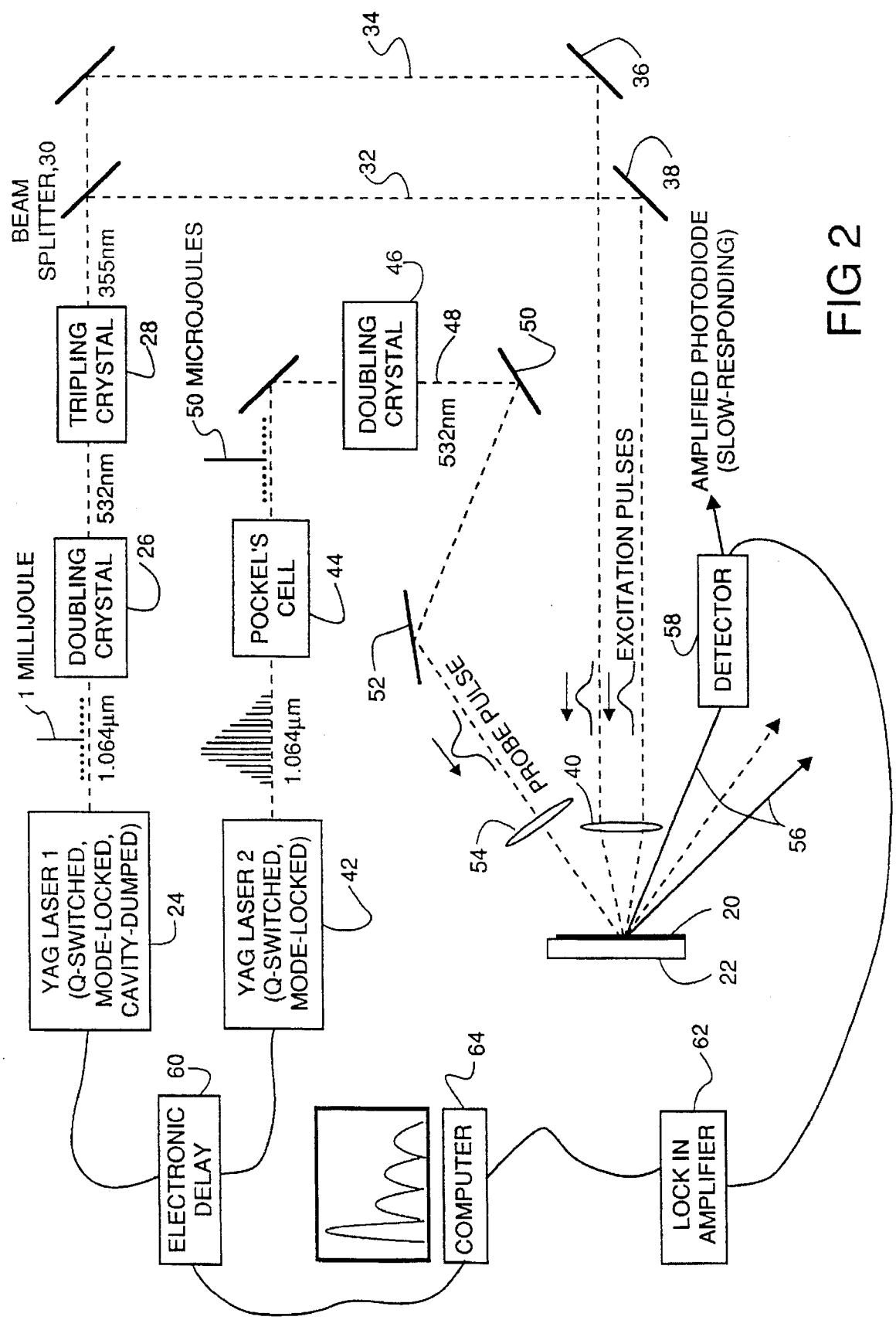

Referring to FIG. 2, an apparatus 2 for measuring the properties of a thin film of polymeric material 20, such as a thin (about 2.2 micron) film of Pyralin® 2555 (a polyimide polymer available from E. I. DuPont de Nemour, Wilmington, Del.; other Pyralin materials may be also available for study, e.g. PI 2525, PI 2545, PI 2611) on a silicon substrate 22, includes a first laser 24 such as a YAG laser that produces a beam at a wavelength of about 1.064 micron and an energy of about 1 millijoule. The pulse width is on the order of picoseconds, in this example 100 psec. The beam is modified by crystals, 26,28 for frequency doubling and tripling to produce an excitation beam wavelength in the ultraviolet at about 355 nanometers. Another preferred wavelength is about 266 nanometers. The beam from the laser is split by a beam splitter 30 into component beams 32, 34 which are directed by reflecting optics 36, 38 toward a focusing element 40 (about 30 cm focal length cylindrical focus) which focuses component beams 32, 34 such that they overlap in time and location within the sample 20. Typically, the spot size on the sample is selected to avoid excessive heating and damage therefrom, e.g., the spot size may be 100 microns to 1 millimeter with an energy of about 10 μJ. In this example, the spot size was about 100 μm high and 2 mm wide (cylindrical focus). The probe laser 42 is a YAG laser for probing the surface morphology by reflectance. The output beam from the laser 42 passes through a Pockel's cell 44 to isolate a particular pulse with an energy of, for example, about 50 microjoules. The probe beam is passed through a doubling crystal 46 to produce a probe pulse 48 having a wavelength generally not absorbed by the sample 20 such as a probe pulse in the visible range, e.g. 532 nm, as in this example. The probe pulse 48 is directed to the sample by optical reflectors 50, 52 and focused by focusing element 54 (about 20 cm focal length) such that the beam impinges upon the sample surface at angle $\theta_I$ about 45° from normal to the unperturbed sample surface. Diffracted beams 56, arising from the morphology at the sample surface, may be detected at angle $\theta_R$ about 45°, by a detector 58 such as an amplified photodiode. The pulses from the excitation laser 24 and probe laser 42 are electronically delayed to probe the surface morphology as a function of time. A delay control 60 times the sequential pulses of the lasers. Typically, the excitation laser pulses at about 1 kilohertz. The probe laser pulses at delay times (from the excitation pulse) varying from the nanosecond range to 40 microseconds or more, depending on the properties of the sample to be determined. The probe pulse width is short relative to the period of the phonon oscillations so that each probe pulse thus represents a single measurement of the instantaneous diffraction signal. The signal detected by the detector 58 is filtered via a lock-in amplifier 62 and passed to an analysis means 64, e.g., a microprocessor, which also receives the pulse delay information and which converts the raw data via Fourier transform to a spectrum of intensity versus frequency.

Referring to FIG. 2a an absorbance spectrum of a thin film of Pyralin® is shown. At the excitation wavelength of 355 nm, the material is highly absorbing. At the probe wavelength of 532 nm, on the other hand, radiation is not substantially absorbed.

Referring to FIG. 2b, the raw LIPS data for the thin Pyralin® sample is shown as a plot of the intensity versus time, being the delay between the excitation beam pulse and the probe beam pulse. In FIG. 2c, the processed data is shown after compilation with the Fast Fourier Transform algorithm (FFT). The analysis time for this measurement was about 10 minutes using about 150,000 excitation and probe pulses. The data may be analyzed to yield material properties as described above.

EXAMPLE 2

Long Probe Pulse

Figure 3:
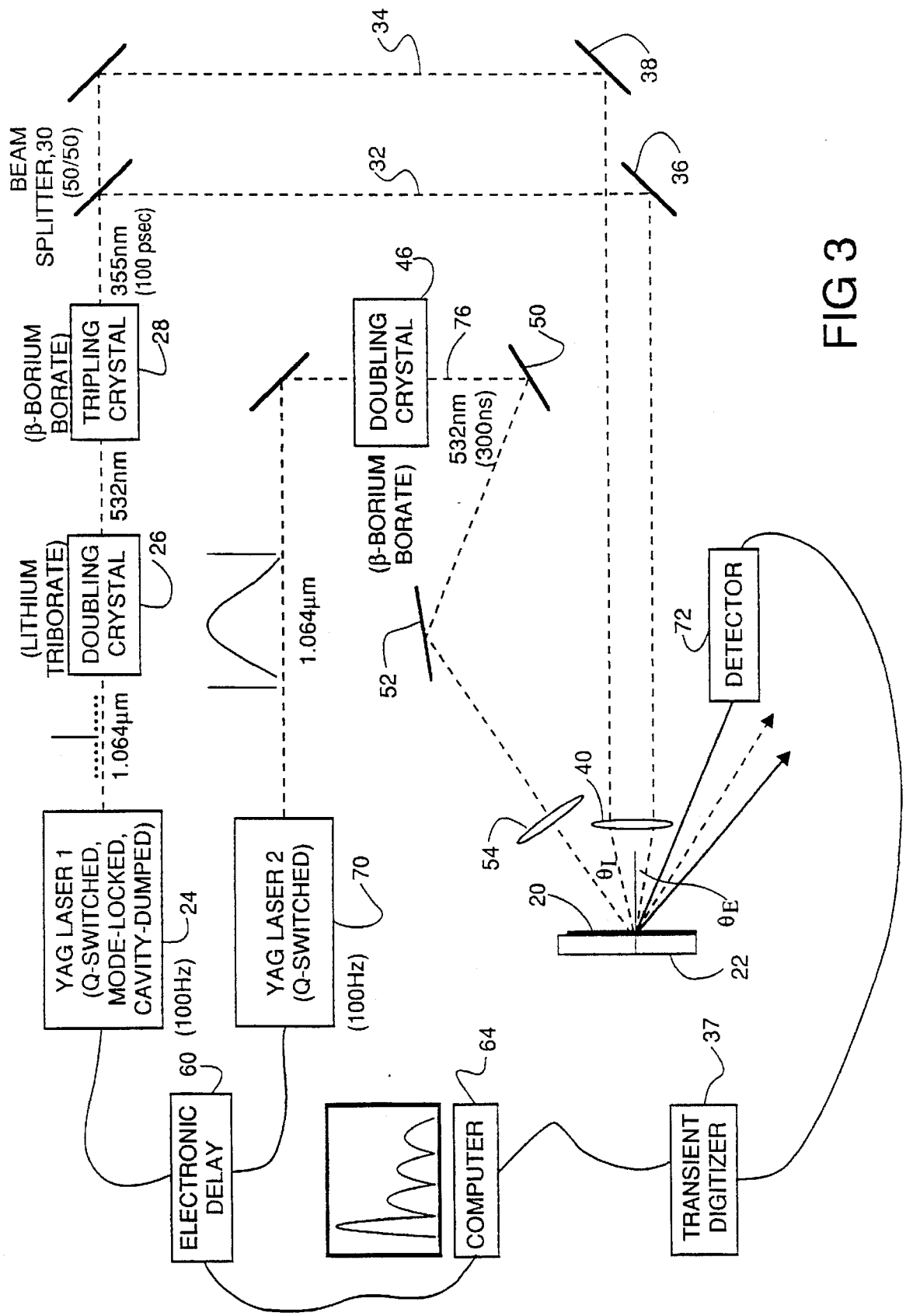

Referring now to FIG. 3, in an alternative mode, a probe laser 70 is adapted to provide a probe beam having a relatively long pulse width such that a substantial time-portion of the transient grating can be measured from each excitation pulse. The probe pulse is typically of longer duration than the excitation probe pulse and may be as long or longer than the detectable diffraction signal from the sample surface. In this example, like numbers refer to the same elements as described in Example 1, FIG. 2. The probe laser 70 may be a YAG laser operated in the Q-switch mode with energy of about 3 millijoules in a pulse width of about 300 nanoseconds. (The peak power, therefore, was on the order of 10,000 watts. Lower power operation, e.g., down to around 1000 watts is believed to be highly practical. Power requirements may be dependent on signal strength which may vary with the sample.) In this case, the probe laser beam 76 impinges upon the sample surface simultaneously with the excitation beams and the full time dependent response from each excitation pulse is recorded. (If signal persists after 300 ns, the probe pulse can be delayed as discussed in Example 1.) The detector 72 is a fast response (370 psec) amplified photodiode (model ARX-SA, Antel Optronics, Inc., 3325B Mainway, Burlington, Ontario, CANADA). The signal is received by a transient digitizer 74 with a 1 GHz bandwidth (digital signal analyzer model 602, Tektronix, Inc., P.O. Box 500, Beaverton, Oreg. 97077). The 1 GHz bandwidth and fast photodetector provide about 1 nsec time resolution, so that acoustic waves of up to 1 GHz frequency can be time resolved. The detector and electronics are generally selected to be as fast as the sample response of interest. A polarizer (thin film) is preferably positioned between lens 54 and the sample.

Referring to FIG. 3a a plot of raw data the transient signal from a single excitation pulse is shown. An advantage of operation in this mode is that, rather than probe a single time point of the transient morphology as in the embodiment of FIG. 2, the diffraction signal from the full duration of the transient morphology produced by each excitation pulse is detected. The time required for signal detection is therefore considerably reduced. FIG. 3a also illustrates the probe pulse profile (which can be subtracted from the raw data prior to processing). In FIG. 3b, the processed data (without subtraction of the probe pulse profile) is shown. This data was collected in about 15 seconds, using about 500 excitation shots, the signals from which were collected and signal averaged. Pyralin films of various thicknesses have been studied, e.g. from about 0.92 to 5.81 micron (spin coated on a 330 micron thick silicon wafer with thickness determined within ±0.05 micron by mechanical stylus profilometer).

Referring particularly to FIG. 3a, the oscillations in the data are due to acoustic oscillations initiated by the crossed excitation pulses. The signal intensity depends on the induced time-dependent material displacements (which are described in more detail in the sections that follow), weighted by the probe pulse intensity envelop which is shown in FIG. 3b. In FIG. 3a, the first part (~85 ns) of the probe pulse arrive at the sample before the excitation pulse, so there is no signal other than that due to parasitically scattered probe light. The excitation pulses heat the sample and initiate acoustic oscillations which are observed in the data. There is also a nonoscillatory component of the signal due to steady-state thermal expansion in the heated regions of the sample. This component finally decays as thermal diffusion washes away the spatially periodic variation in sample temperature. Thermal decay is not observed in these experiments because at these wavevectors, the timescale for thermal diffusion is much longer than the length of the Q-switched probe pulse. Instead, the signal in FIG. 3a disappears as the probe pulse ends. (As discussed below, with a larger temporal probe pulse, such as a CW probe pulse, longer sample excitation signals may be detected.)

Figures 3C, 3D:
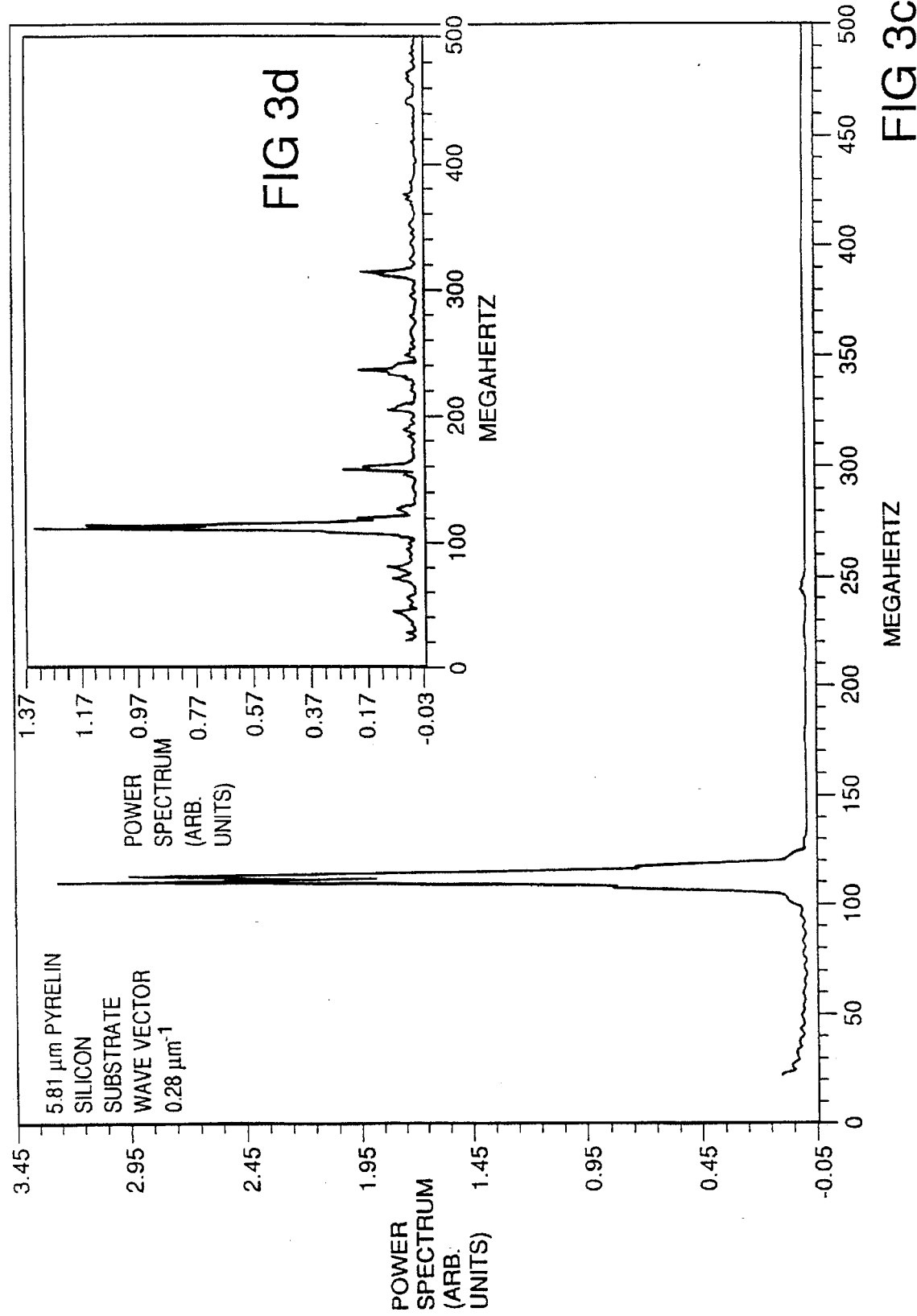

From the data in FIG. 3a, the frequency of the surface acoustic wave can be extracted. In the Fourier transform of the data shown in FIG. 3c, the acoustic response is dominated by one mode with a frequency of 113±2 MHz. The dc component of the transform (not shown) is 30 times larger than the acoustic peak. In FIG. 3d the Fourier transform of diffracted signal is shown taken under identical conditions as the data in FIG. 3a, but with only one laser shot, i.e., no averaging. While this spectrum is noisier than the spectrum of the averaged data, the position of the main peak is identical. (The extra noise seen in FIG. 3d is believed to be due to self-modelocking within the one Q-switched probe pulse.) The data clearly illustrates the ability to perform true one-laser shot experiments. Best results can be obtained with a smooth probe pulse temporal profile.

In FIGS. 4 and 4a, ISTS raw data and its Fourier transform, are shown respectively for the same sample at a larger scattering wavevector. It can clearly be seen that there are at least two surface acoustic modes which contribute to the signal.

To insure that the signal was due to the polyimide film, control experiments were performed on uncoated silicon wafers. No signal from the silicon surface could be detected.

Further, it is possible to distinguish between scattering due to modulation of the dielectric constant through elasto-optic coupling and diffraction due to surface and interface ripple through analysis of the polarization properties of the diffracted light and the acoustic wavevector dependence of the diffracted signal intensity. Pseudo-Rayleigh waves have both transverse and longitudinal character, and therefore give rise to modulation of both diagonal and off-diagonal elements of the dielectric tensor of a thin film through elasto-optic coupling. If elasto-optic coupling is a significant source of diffraction, then a component of the diffracted probe beam should be polarized at an angle 90° relative to the incident probe beam (depolarized or VH scattering). The magnitude of this component relative to the non-depolarized diffracted component depends on the square of the ratio of off-diagonal to the diagonal elasto-optic coupling coefficients. By contrast, for a coplanar scattering geometry surface ripple does not rotate the polarization of the diffracted light.

In addition, if elasto-optic coupling were the dominant diffraction mechanism, the signal intensity would be independent of scattering wavevector q since the acoustic strain induced through bulk ISTS excitation is q-independent. By contrast, surface ripple arises from components of the acoustic displacement rather than strain and should thus vary as $q^{-1}$. Signal from surface ripple depends on the square of the displacement, and as detailed below the signal intensity due to surface ripple decreases approximately as $q^{-2}$.

In experiments performed above, no depolarized component of the diffracted signal was detected. It was also observed that the diffracted signal intensity decreases sharply as the q is increased. This indicates that the diffracted signals are due predominantly to surface and interface ripple induced by the pseudo-Rayleigh waves.

EXAMPLE 3

CW Probe

A further embodiment employs a continuous wave probe pulse from, e.g., a CW argon laser generating a CW beam of known duration in place of the YAG laser in Example 2. The probe laser wavelength may be in the visible, 514 nm, and probe pulse width controlled by an EO modulator (in place of the doubling crystal shown in FIG. 3). (No electronic delay is necessary for the CW experiments.) This embodiment, similar to that of Example 2, allows the transient response from each excitation shot to be completely detected. In this method the probe beam has a time-independent profile, thus enabling reduction in noise contribution when subtracting the probe beam profile from the detected signal.

Figure 5:
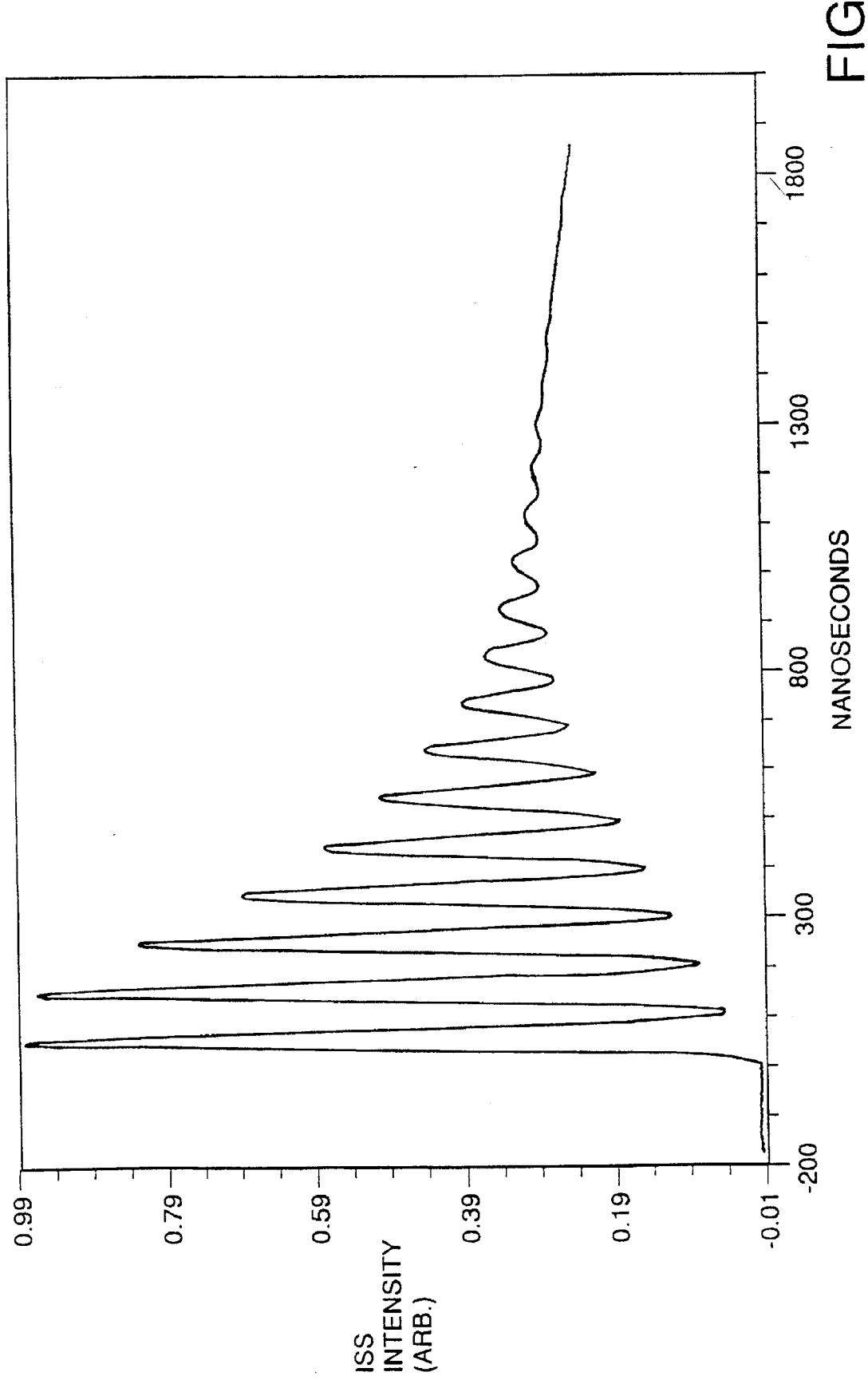
Figure 5A:
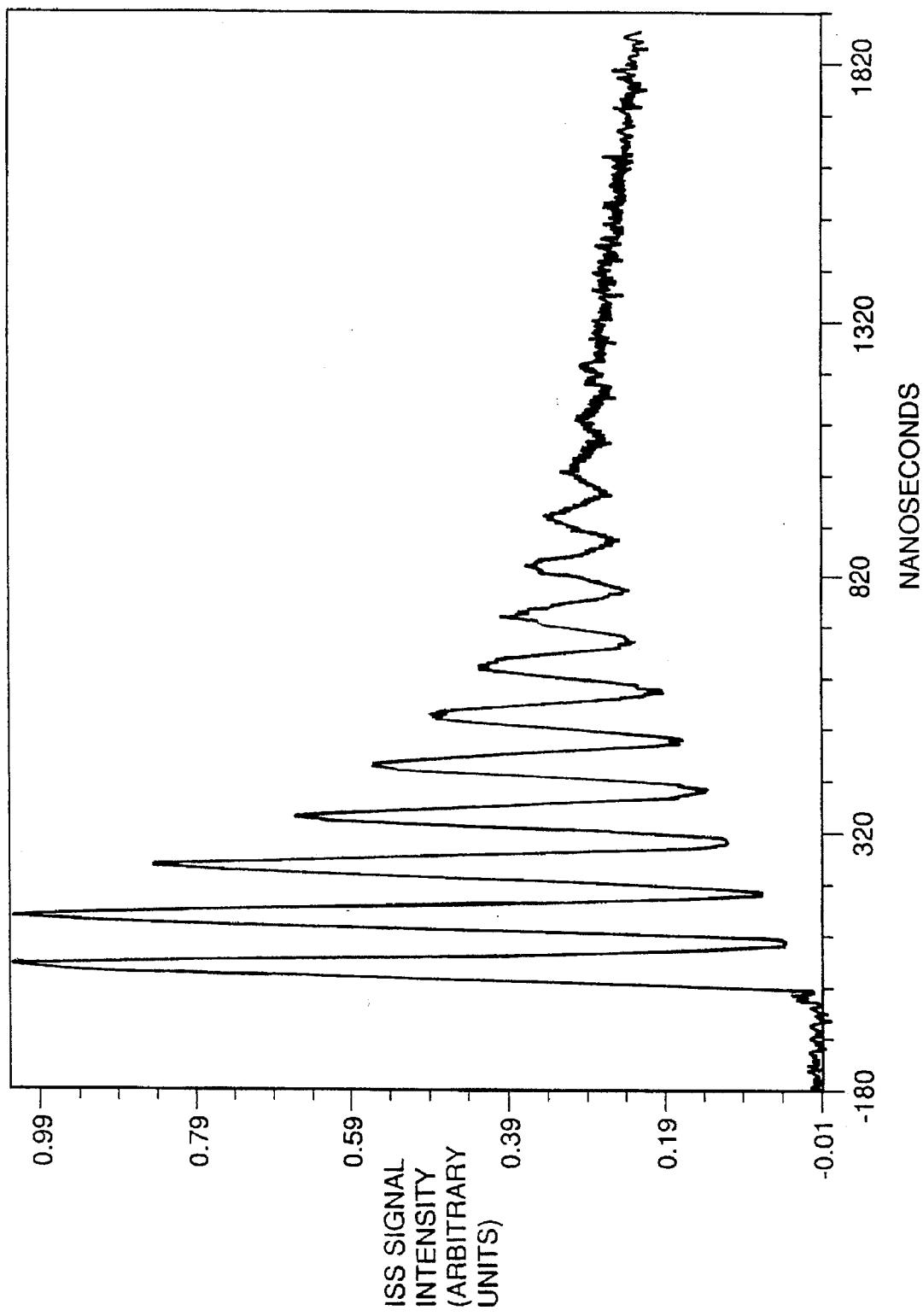
FIG. 5a is a plot similar to FIG. 5 but from a single excitation shot.

Referring to FIGS. 5 and 5a, raw data from an unsupported polyimide film using a YAG laser excitation source at λ=266 nm, 100 psec (a quadrupling crystal is used in place of tripling crystal 28) and a gated (500 μsec) small frame argon ion CW probe (about 50–100 micron beam size, with single line power of about 1 watt) is illustrated for 200 signal averaged excitation shots and a single excitation shot, respectively. Despite the relatively low intensity, about 50 to 100 times lower than the Q-switched probe used in the experiments above, good data was obtained. Care should be taken to efficiently gate the beam to avoid overexposure which can lead to damage of the sample. In these experiments, a Q-polarizer was placed before the EO gate.

Figure 6:
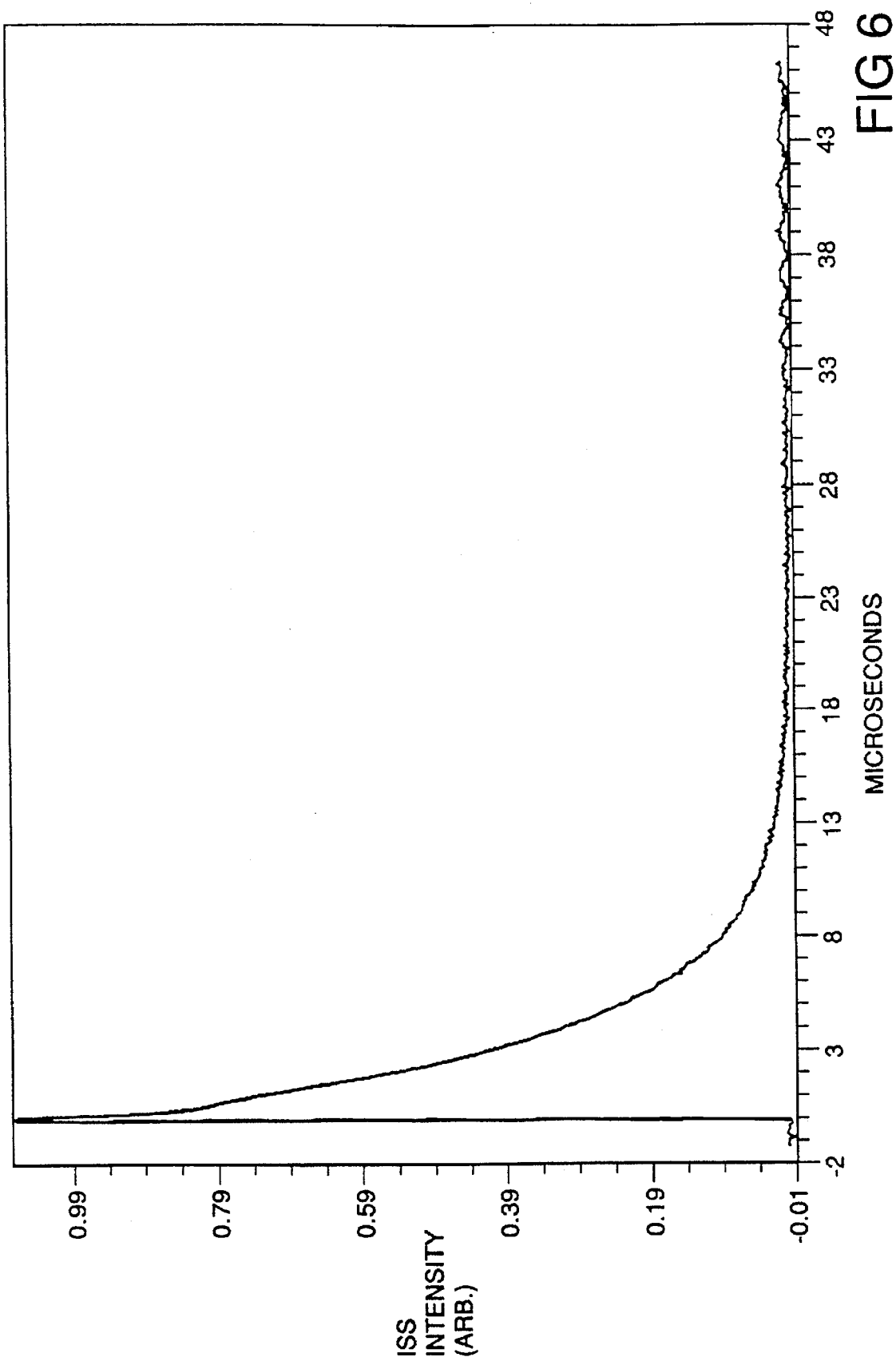
FIG. 6 is a plot of intensity versus time, raw data, from an experimental set up using a CW probe laser to obtain thermal data.

An advantage of the gated CW probe is that thermal process which occur on timescales larger than acoustic processes can be efficiently monitored. Likewise, the long temporal widths available with the CW probe allows the entirety of the sample acoustic profile to be detected. In addition, by including frequency dependent loss modulus, the experiments can account for acoustic dampings. Referring to FIG. 6, a thermal decay curve of the polyimide sample over a microsecond time scale is shown. Similar data can be obtained from a single excitation shot.

Theoretical Treatment and Parameter Optimization

A discussion of the features of the data obtained and a theoretical analysis that leads to optimization of the experiment for detecting signal predominately from the induced surface ripple, follows.

In ISTS, two ultrashort laser excitation pulses are crossed temporally and spatially at the sample. An optical interference pattern characterized by scattering wavevector q is formed, where q is the difference between the wavevectors of the crossed pulses. The scattering wavevector magnitude q associated with each excitation angle $\theta_E$ can be calculated according to:

$$q = \frac{4\pi \sin\left(\frac{\theta_E}{2}\right)}{\lambda} \quad (1)$$

where λ is the wavelength of the excitation light. Experimentally, referring particularly to the data obtained in the experiments performed as discussed with respect to FIG. 3 et seq., data can be recorded as a function of the excitation angle θ for all the Pyralin/Si sample thicknesses. The angles used in this study are 0.48°, 0.68°, 0.72°, 0.92°, 1.07°, 1.17°, 1.62° 1.67°, 1.77°, 1.93°, 2.37°, 3.40°, 3.92°, and 5.85°. (These angles may be measured mechanically using a calibrated rotation stage and are accurate to ±0.05°.) The corresponding scattering wavevectors according to (a) are 0.15, 0.21, 0.22, 0.28, 0.33, 0.36, 0.50, 0.52, 0.55, 0.60, 0.73, 1.05, 1.21, and 1.81 inverse microns. These are accurate to ±0.01 inverse microns. The wavevectors were chose to lie along a crystal axis of the silicon substrate. However, experiments performed with a wavevector magnitude of 0.52 μm$^{-1}$ on a 5.81 μm Pyralin film sample showed no dependence on wavevector direction.

I. Surface Ripple Amplitude

An order of magnitude estimate can be made for the surface ripple generated in an ISTS experiment by calculating the magnitude of the temperature grating set up by the excitation laser pulses and then relating this to a displacement amplitude using the linear thermal expansion coefficient. The temperature change ΔT for light impinging on the surface (in the y=−h plane) in the y direction and setting up a grating of wavevector q in the z direction can be written as in eqs (2–3).

$$\Delta T(y,z) = Ae^{-\zeta y}[1 + e^{iqz}] \quad (2)$$

$$A = \frac{1}{\rho C} P_a(1-R)I_E \zeta e^{-\zeta h} \quad (3)$$

Here, 2.303ζ is the material absorption coefficient, $I_E$ is the total energy per unit area of the excitation laser pulses, ρ is the mass density, C is the heat capacity per unit mass, R is the reflectivity for the material/air interface and $P_a$ is the fraction of absorbed light that is converted to heat. An upper limit for the average value of the temperature increase over the thickness of the film can be estimated with (2) by setting $P_a$=1 and R=0. For these experiments, $I_E$=1 6 mJ/cm$^2$ and ζ=1.3 μm$^{-1}$. Using values of ρ=1 g/cm$^3$ and C=2.3 J/(g.K) which are typical for polymers leads to an average temperature increase of approximately 8 K for a 4 μm thick film.

This temperature change can be related to the change in the y-direction length of a volume element $\delta L_y(y,z)$ using the linear thermal expansion coefficient $\alpha_T$ as in eq. (4).

$$\delta L_y(y,z) = \alpha_T \Delta T(y,z) dy \quad (4)$$

For the general case, the total surface ripple $R_{rip}(z)$ can be found by integrating this expression over the sample thickness. For a thin film of thickness h attached to a nonabsorbing substrate as in these experiments the integration extends only over the thickness of the film. Performing this integration leads to eq. (5).

$$R_{rip}(z) = \frac{1}{\rho C} P_a(1-R)I_E(1-e^{-\zeta h})\alpha_T[1+e^{iqz}] \quad (5)$$

Using a typical polymeric value of $\alpha_T$=80×10$^{-6}$m/(m.K)$^{16}$ for the linear thermal expansion coefficient yields an upper-limit estimate of 0.005 microns for the surface corrugation amplitude excited by ISTS. This estimation assumes that neighboring volume elements slide by one another, and does not consider the effects of stress that will tend to reduce the corrugation. For this reason, expression (5) does not show the expected 1/q dependence.

II. Theory

In order to extract the elastic constants of the thin film from the pseudo-Rayleigh mode frequencies measured at different scattering wavevector magnitudes q, the dispersion of ω(q) for the various modes is to be understood. In fact, the frequency depends only on the product qh, where h is the film thickness, so that the results of measurements on films of different thickness can be compared. As mentioned earlier, the ISTS excitation efficiencies and the probe diffraction efficiencies for each of the modes are to be determined. The ISTS signal expected from a supported film is derived below treating the excitation then the probing process. An isotropic theory is used since no effects of the elastic anisotropy of silicon or the film were observed.

A. ISTS Excitation of the System

Starting with the equations of thermoelasticity for an isotropic, elastic, and homogeneous medium:

$$c_{44}\nabla^2 u + (c_{11}-c_{44})\nabla(\nabla \cdot u) = \gamma \nabla T + \rho \frac{\partial^2 u}{\partial t^2} \tag{6}$$

$$\kappa \nabla^2 T - C_s \rho \frac{\partial T}{\partial t} - \eta \kappa \nabla \cdot \frac{\partial u}{\partial t} = -Q \tag{7}$$

In these expressions u is a vector describing the material displacements, T is the fluctuation in temperature relative to the equilibrium temperature, $\rho$ is the equilibrium density, and $c_{44}$ and $c_{11}$ are the elastic constants which are related to the bulk longitudinal and transverse acoustic velocities according to $V_L=(C_{11}/\rho)^{1/2}$ and $V_T=(C_{44}/\rho)^{1/2}$. $\gamma$ is a constant related to the elastic constants and the coefficient of linear volume expansion $\alpha_T$ by $\gamma=(3c_{11}-4c_{44})\alpha_T$. $\kappa$ is the thermal conductivity, $\eta=\gamma T_e/\kappa$ and $C_s$ is the constant strain specific heat per unit mass. Finally, Q represents the absorbed heat per unit time per unit volume derived from the excitation laser pulses.

If u is expressed in terms of longitudinal ($\Phi$) and transverse ($\Psi$) potentials, $$u=\nabla\phi+\nabla\times\psi \nabla\psi=0 \tag{8}$$

then equations (6) and (7) can be rewritten as follows.

$$\kappa \nabla^2 T - C_s \rho \frac{\partial T}{\partial t} = -Q \tag{9}$$

$$\nabla^2 \phi - \frac{1}{c_{11}} \frac{\partial^2 \phi}{\partial t^2} = \frac{\gamma}{\rho c_{11}} T \tag{10}$$

$$\nabla^2 \psi - \frac{1}{c_{44}} \frac{\partial^2 \psi}{\partial t^2} = 0 \tag{11}$$

It is assumed that longitudinal compressions do not cause substantial changes in temperature ($\eta\sim 0$ in eq. (7)).

Note that for a bulk system, the last two equations describe uncoupled longitudinal and transverse acoustic modes respectively. Since the laser heating enters through eq. (9) which is only directly coupled to eq. (10), ISTS only excites longitudinal acoustic modes in bulk isotropic systems. However, this simple picture breaks down for a thin film, since boundary conditions must be satisfied. In particular, for a thin film in intimate contact with a substrate, the material displacements and the normal components of the stress must be continuous across the interface and the normal components of the stress at any free surface must vanish. These boundary conditions lead to coupling between the longitudinal and transverse potentials so that every surface acoustic mode has both longitudinal and transverse character.

Figure 7:
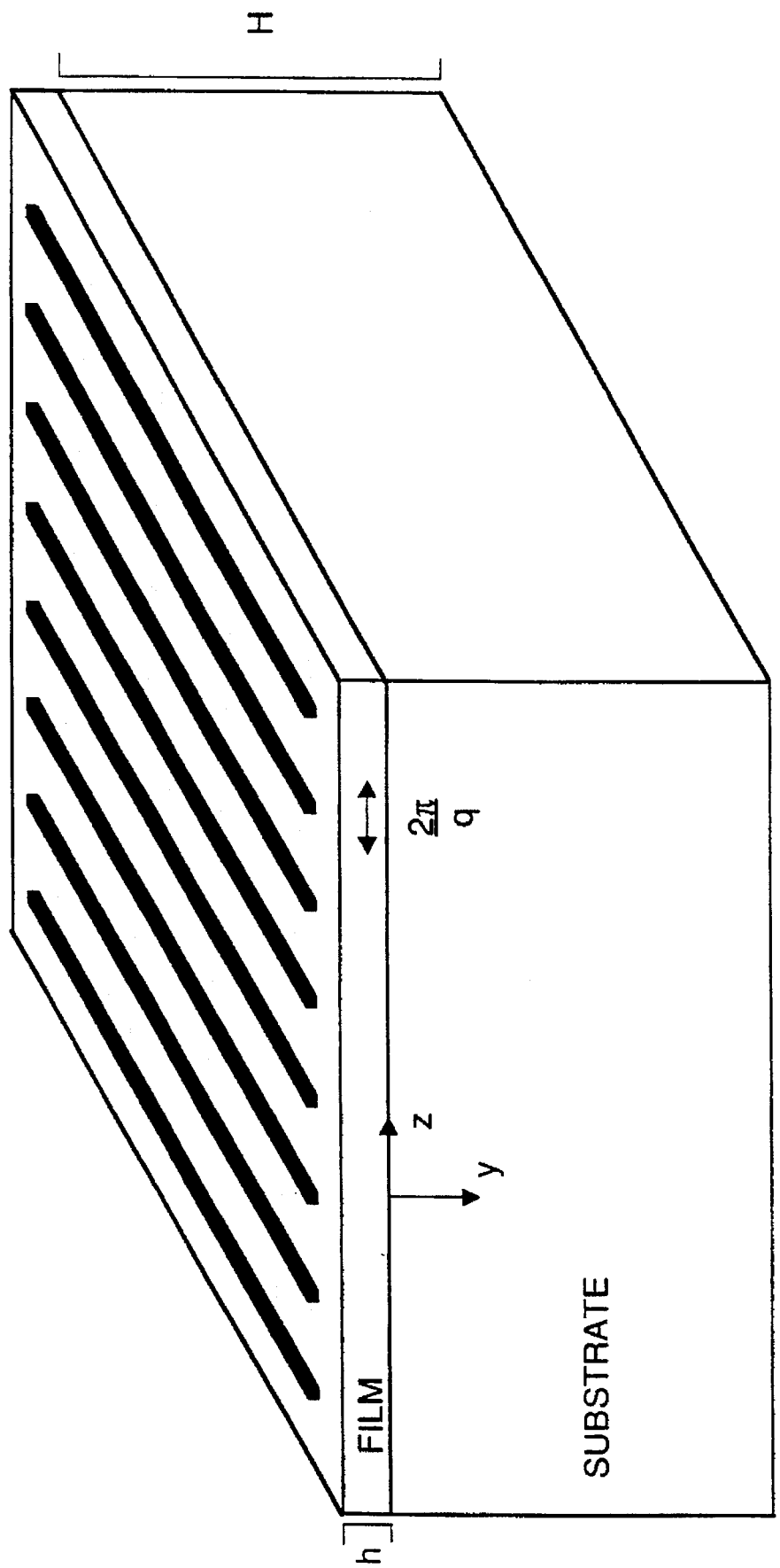
FIG. 7 illustrates the system geometry used in the theoretical calculations, wherein the film fills the space between y=0 and y=−h and the substrate fills the area from y=0 to y=+H and the acoustic wavevector set up by the pump beams is in the z direction.

The film/substrate system geometry is depicted in FIG. 7. The substrate fills the region from y=0 to y=+H and the film fills the region from y=0 to y=-h. It is assumed that the ISTS excitation beams form an infinite uniform grating pattern with wavevector q in the z direction which is independent of x and damped along y due to optical absorption. In this analysis, H is considered infinite so that the substrate fills the whole y>0 half space. (The corrections that occur when the finite size of the substrate is explicitly accounted for is discussed below.)

The first step in solving equations (9)–(11) is to determine the temperature distribution set up by the excitation pulses. The dynamics of thermal diffusion take place on a much longer timescale than the acoustic dynamics. Thus, for analyzing the excitation of the film-substrate system, $\kappa$ can be set to zero in eq. (9). In ISTS, the excitation laser pulse duration is short compared to the acoustic oscillation period. Here it is assumed that conversion of optical energy to heat through molecular electronic and vibrational relaxation also occurs on a fast time scale relative to the acoustic oscillation period so that the time dependence of Q in eq. (9) can be approximated by a delta-function at zero time. More gradual thermalization will reduce all the acoustic amplitudes but should not affect the relative amplitudes of the different modes substantially. Equation (9) is solved for the temperature distribution set up by the laser excitation beams to yield eq. (12).

$$T(y,z,t)=Ae^{-\zeta(y+h)}[1+e^{iqz}]\theta(t) \tag{12}$$

Here, $\theta(t)$ is the Heaviside step function which turns on at t=0, and A and $\zeta$ were introduced in eqs (2–3). Since the film absorbs strongly and the silicon substrate reflects the 355 nm excitation light used in these experiments, T(y,z,t) is only nonzero in the film (for –h<y<0).

With this functional form for the temperature distribution, equations (10) and (11) can be solved using transform techniques. Since the temperature distribution is independent of x, all derivatives with respect to x are neglected. From the geometry of the system and the nature of the temperature distribution given in (12), a Laplace transform for the time variable and exponential Fourier transform for the z coordinate are the natural choices. The transformed solutions for the potentials $\phi$ and $\psi$ are then found to be, $$\phi(k,y,s) = \begin{cases} A_\phi(k,s)\exp\left(y\sqrt{k^2+\frac{s^2}{v_{Lf}^2}}\right) + B_\phi(k,s)\exp\left(-y\sqrt{k^2+\frac{s^2}{v_{Lf}^2}}\right) \\ + \frac{A\gamma}{\rho s} e^{-\zeta y}\left[\frac{\delta(k)}{-s^2+\zeta^2 v_{Lf}^2} + \frac{\delta(k-q)}{-k^2 v_{Lf}^2 + \zeta^2 v_{Lf}^2 - s^2}\right] \quad -h<y<0 \\ C_\phi(k,s)\exp\left(y\sqrt{k^2+\frac{s^2}{v_{Ls}^2}}\right) + D_\phi(k,s)\exp\left(-y\sqrt{k^2+\frac{s^2}{v_{Ls}^2}}\right) \quad H>y>0 \end{cases} \tag{13}$$

-continued $$\psi(k,y,s) = \begin{cases} A_\psi(k,s)\hat{x}\exp\left(y\sqrt{k^2+\frac{s^2}{v_{Tf}^2}}\right) + B_\psi(k,s)\hat{x}\exp\left(-y\sqrt{k^2+\frac{s^2}{v_{Tf}^2}}\right) & -h < y < 0 \\ C_\psi(k,s)\hat{x}\exp\left(y\sqrt{k^2+\frac{s^2}{v_{Ts}^2}}\right) + D_\psi(k,s)\hat{x}\exp\left(-y\sqrt{k^2+\frac{s^2}{v_{Ts}^2}}\right) & H > y > 0 \end{cases} \quad (14)$$

where k is the Fourier transform variable conjugate to z and s is the Laplace variable conjugate to time (+). In these expressions, 'Lf, 'Tf, 'Ls, and 'Ts are the bulk longitudinal and transverse velocities in the film and substrate respectively. In taking the Laplace transform, the initial conditions that there is no displacement or motion at t=0 when the laser pulses first arrive at the sample have been used. Note that choosing the only nonzero component of ψ to lie along the x axis allows for trivial satisfaction of the gauge ∇·ψ=0 used here. Finally, all but the third term in the expression for the longitudinal potential in the film are homogeneous solutions to the equations of motion. This third term is the particular solution of equation (10) and can be thought of as driving the motion of the film and giving rise to a response consisting of a longitudinal disturbance propagating along z, a periodic stress pulse propagating along y, and a dc response.

The variables $A_\phi(k,s)$, $B_\phi(k,s)$, $D_\phi(k,s)$ etc. are potential constants which are determined by imposing the necessary boundary conditions and physical realizability requirements.

For the system of FIG. 7 with H infinite, the terms involving $C_\phi(k,s)$ and $C_\phi(k,s)$ represent physically unreasonable solutions. For this reason, they are set to zero. The other six constants are determined with the boundary conditions. As stated earlier, these are that u and the normal components of the stress are continuous at y=0 and that the normal components of the stress vanish for y=−h. The stress tensor is calculated using the Duhamel-Neumann relation shown in eq. (15) in order to properly take into account the contribution from the temperature grating.

$$\sigma_{ij} = c_{44}\left(\frac{\partial u_i}{\partial x_j} + \frac{\partial u_j}{\partial x_i}\right) + [(c_{11} - 2c_{44})\nabla \cdot u - \gamma T]\delta_{ij} \quad (15)$$

Using equations (8), (15) and (12)–(14), the boundary conditions can be imposed. The six relations thus derived are most conveniently expressed in matrix form.

$$CD = F \quad (16)$$

$$C = \begin{pmatrix} (1+p^2)e^{-nkh} & (1+p^2)e^{nkh} & 2ipe^{-pkh} & -2ipe^{pkh} & 0 & 0 \\ 2ine^{-nkh} & -2ine^{nkh} & -(1+p^2)e^{-nkh} & -(1+p^2)e^{nkh} & 0 & 0 \\ 1+p^2 & 1+p^2 & 2ip & -2ip & -(1+r^2)g & 2irg \\ 2in & -2in & -(1+p^2) & -(1+p^2) & 2img & (1+r^2)g \\ -1 & -1 & -ip & ip & 1 & -ir \\ in & -in & -1 & -1 & im & 1 \end{pmatrix} \quad (17)$$

$$D = \begin{pmatrix} A_\phi \\ B_\phi \\ A_\psi \\ B_\psi \\ D_\phi \\ D_\psi \end{pmatrix} \quad (18)$$

$$F = \frac{iA\gamma}{v_{Tf}^2 \rho k v} \begin{pmatrix} \frac{-(\delta(k)+\delta(k-q))}{k^2} + \frac{v_{Lf}^2}{k^2}\left(\frac{-(v_{Lf}^2 - 2v_{Tf}^2)}{v_{Lf}^2} + \frac{\zeta^2}{k^2}\right) & \left(\frac{\delta(k)}{v^2 + \frac{v_{Lf}^2\zeta^2}{k^2}} + \frac{\delta(k-q)}{v^2 + v_{Lf}^2\left(\frac{\zeta^2-k^2}{k^2}\right)}\right) \\ \frac{2\zeta v_{Tf}^2}{ik^3}\left(\frac{\delta(k)}{v^2 + \frac{v_{Lf}^2\zeta^2}{k^2}} + \frac{\delta(k-q)}{v^2 + v_{Lf}^2\left(\frac{\zeta^2-k^2}{k^2}\right)}\right) \\ \frac{-e^{-\zeta d}(\delta(k)+\delta(k-q))}{k^2} + \frac{e^{-\zeta d}v_{Lf}^2}{k^2}\left(\frac{-(v_{Lf}^2-2v_{Tf}^2)}{v_{Lf}^2} + \frac{\zeta^2}{k^2}\right) & \left(\frac{\delta(k)}{v^2 + \frac{v_{Lf}^2\zeta^2}{k^2}} + \frac{\delta(k-q)}{v^2 + v_{Lf}^2\left(\frac{\zeta^2-k^2}{k^2}\right)}\right) \\ \frac{2e^{-\zeta d}\zeta v_{Tf}^2}{ik^3}\left(\frac{\delta(k)}{v^2 + \frac{v_{Lf}^2\zeta^2}{k^2}} + \frac{\delta(k-q)}{v^2 + v_{Lf}^2\left(\frac{\zeta^2-k^2}{k^2}\right)}\right) \end{pmatrix} \quad (19)$$

$$\left. \begin{array}{c} \dfrac{-e^{-\zeta d}v_{Tf}^2}{k^2}\left(\dfrac{\delta(k)}{v^2+\dfrac{v_{Lf}^2\zeta^2}{k^2}}+\dfrac{\delta(k-q)}{v^2+v_{Lf}^2\left(\dfrac{\zeta^2-k^2}{k^2}\right)}\right) \\[20pt] \dfrac{e^{-\zeta d}v_{Tf}^2}{k^3}\left(\dfrac{\delta(k)}{v^2+\dfrac{v_{Lf}^2\zeta^2}{k^2}}+\dfrac{\delta(k-q)}{v^2+v_{Lf}^2\left(\dfrac{\zeta^2-k^2}{k^2}\right)}\right) \end{array} \right\} \quad (20)$$

$$n = \sqrt{1 - \frac{v^2}{v_{Lf}^2}} \qquad (21)$$

$$p = \sqrt{1 - \frac{v^2}{v_{Tf}^2}} \qquad (22)$$

$$m = \sqrt{1 - \frac{v^2}{v_{Ls}^2}} \qquad (23)$$

$$r = \sqrt{1 - \frac{v^2}{v_{Ts}^2}}$$

$$g = \frac{\rho_s v_{Ts}^2}{\rho_f v_{Tf}^2} \qquad (24)$$

and $\rho_f$ and $\rho_s$ are the densities in the film and substrate respectively. The first two rows of the matrix equation ensure that the yy and the yz components of the stress respectively are zero at the surface of the film. The next two rows require continuity of the yy and yz components of the stress respectively at the interface. Finally, the last two rows require that the z and y components of the material velocities respectively are continuous at the interface. For notational convenience, the k and s dependence of the potential constants has been dropped. Also, the Laplace variable s has been written as $s^2 = -\omega^2 = -v^2 K^2$ where w is the real frequency and v is the velocity of the acoustic mode solutions. This transformation limits the possible solutions to strictly pseudo-Rayleigh modes with velocities below the transverse velocity of the substrate. A continuum of "leaky mode" solutions with complex frequency are also possible for velocities greater than $V_{Ts}$. These solutions are damped as energy is "lost" to the semi-infinite substrate. Normal mode solutions of eq. (16) occur when $$\det(\underline{C}) = 0 \qquad (25)$$

Aside from kh and v, the matrix $\underline{c}$ only contains constants related to the film and the substrate. All of the laser and optical properties appear in the column matrix F. Thus, eq. (25) can be solved to yield the dispersion relations (qh vs. v where q is the acoustic wavevector) for the various pseudo-Rayleigh modes irrespective of the ISTS excitation source.

An example of typical dispersion curves for the substrate loading case (ie. "Ts>"Tf) is shown for the lowest 16 modes in FIG. 8. As qh approaches zero only one mode, whose velocity approaches only one mode whose velocity approaches that of the substrate pure Rayleigh mode 'Rs, exists. At large qh, this lowest mode approaches the pure Rayleigh surface mode of the film with velocity 'Rf. Each of the higher velocity modes, often called Sezawa modes, has a limiting qh value below it does not propagate. At this qh value, the velocity of each mode is equal to the substrate transverse velocity "Ts. As shown in FIG. 8, as qh is increased, these modes all asymptotically approach the film transverse velocity.

In order to solve for the displacements of a particular mode j excited through ISTS, one must solve the full eq. (16) for the potential constants at the qh value and velocity of interest. It can be shown using eqs. (8) and (13–14) that the normal mode displacements $u^j$ with wavevector q obey the following equation $$u^j(q,y,z,t) = [u_y^j(q,y)\hat{y} + u_z^j(q,y)\hat{z}]e^{iqz}e^{iv_jqt} \qquad (26)$$

where $$u_y^j(q,y) = \begin{cases} qn_j[\overline{A}_\phi^j e^{yqn_j} - \overline{B}_\phi^j e^{-yqn_j}] + iq[\overline{A}_\psi^j e^{yqp_j} + \overline{B}_\psi^j e^{-yqp_j}] & -h < y < 0 \\ -qm_j\overline{D}_\phi^j e^{-yqm_j} + iq\overline{D}_\psi^j e^{-yqr_j} & y > 0 \end{cases} \qquad (27)$$

$$u_z^j(q,y) = \begin{cases} iq[\overline{A}_\phi^j e^{yqn_j} - \overline{B}_\phi^j e^{-yqn_j}] + qp_j[-\overline{A}_\psi^j e^{yqp_j} + \overline{B}_\psi^j e^{-yqp_j}] & -h < y < 0 \\ iq\overline{D}_\phi^j e^{-yqm_j} + qr_j\overline{D}_\psi^j e^{-yqr_j} & y > 0 \end{cases} \qquad (28)$$

In these expressions, the tildes denote the residue of the quantity evaluated at the appropriate pole. Note that the material displacements oscillate with frequency $\omega_j = v_j q$. Examples of the pseudo-Rayleigh displacements for various modes at one qh value are showing in FIG. 8. The total displacements at a particular wavevector and sample thickness will be the sum of the uj values for each pseudo- Rayleigh mode plus a nonoscillatory term due to steady-state thermal expansion.

B. Probe Diffraction

In this section, an analysis is presented of diffraction appropriate for the ISTS experiments described here in which ripple effects were found to dominate. The equations below are the reflected and transmitted first order diffracted components of light from a corrugated half space, modified to deal with the case of arbitrary indices of refraction on either side of the corrugated interface, and to the case of standing wave corrugation. In addition, index modulation contributions to the phase are neglected. The results are, represent the probe and diffracted beam paths for the two final signal directions seen experimentally. The first three paths show the components involving diffraction from the film surface ripple. The fourth path describes the component arising from diffraction from the interface ripple. In general, all four components contribute to the diffracted signal in the two signal directions.

The electric fields at the detector associated with these four diffraction contributions can be obtained using eqs. (29–30), Snell's Law, and taking into account reflective losses at the film-air interface. In the following, it is assumed that all light striking the film-substrate interface is reflected.

$$E_r = \mp a \sqrt{I_o} \; e^{i\omega x} e^{-in_1 k_i R_o} J_1(\alpha_1) \left( \frac{(1+r(\theta_i))\cos\theta_d - (1-r(\theta_i))\cos\theta_1}{2\cos\theta_i} \pm \frac{q(1+r(\theta_i))(\sin\theta_d + \sin\theta_i)}{2 n_1 k_i \cos\theta_i (\cos\theta_d + \cos\theta_i)} \right) \tag{29a}$$

$$\alpha_1 = \delta(t) n_1 k_i (\cos\theta_d + \cos\theta_i) \tag{29b}$$

$$\sin\theta_{d\pm1} = \sin\theta_i \pm \frac{q}{n_1 k_i} \tag{29c}$$

$$E_t = \mp a \sqrt{I_o} \; e^{i\omega x} e^{-in_2 k_i R_o} J_1(\alpha_1') \left( \frac{(1+r(\theta_i)) \frac{n_2}{n_1} \cos\theta_t + (1-r(\theta_i))\cos\theta_i}{2\cos\theta_i} \mp \frac{q(1+r(\theta_i)) \left( \frac{n_2}{n_1} \sin\theta_t + \sin\theta_i \right)}{2 n_1 k_i \cos\theta_i \left( \frac{n_2}{n_1} \cos\theta_t + \cos\theta_i \right)} \right) \tag{30a}$$

$$\alpha_1' = \delta(t) n_1 k_i \left( \frac{n_2}{n_1} \cos\theta_t - \cos\theta_i \right) \tag{30b}$$

$$\sin\theta_{t\pm1} = \frac{n_1}{n_2} \sin\theta_i \pm \frac{q}{n_2 k_i} \tag{30c}$$

In these equations, $I_o$ is the intensity of the probe measured in medium 1, and $k_i$ is the wavevector of the probe measured in vacuum. $\theta_i$ is the angle of the probe relative to the corrugated interface, a is the unit vector representing the polarization of the probe, r is the reflection coefficient for transmission from medium 1 to medium 2, and $R_o$ is the distance from the point at which the diffraction is generated to the detector. Also, q is the wavevector of the corrugation, and $\delta(t)$ is the time dependent amplitude of the corrugation. Finally, the upper signs refer to the +1 diffracted order, while the lower signs refer to −1 diffracted order.

For a thin supported film, there are four sources of first order ripple diffraction which must be considered. These are shown schematically in FIG. 9. Parts A and B of this figure In addition, due to the spatial size of the probe pulse, the thickness of the film, the index of refraction of the film, the wavevector of the corrugation, and the angle of incidence, it is a good approximation to assume that all of the diffracted beams give in FIG. 9a or 9b emerge from the same point on the film and travel parallel to one another. The results, written in terms of sums over pseudo-Rayleigh mode amplitudes, are shown in the following equations.

$$E_1 = +a \sqrt{I_o} \; K_1 e^{i\omega x} e^{-ik_i R_o} \sum_{j=0}^{N} u_j j(q, y = -h) \sin(v_j q t) \tag{31a}$$

$$K_1 = k_1 (\cos\theta_d + \cos\theta_i) \left[ \frac{(1+r(\theta_i))\cos\theta_d - (1-r(\theta_i))\cos\theta_i}{4\cos\theta_i} \pm \frac{q(1+r(\theta_i))(\sin\theta_d + \sin\theta_i)}{4 k_i \cos\theta_i (\cos\theta_d + \cos\theta_i)} \right] \tag{31b}$$

$$\sin\theta_{d\pm1} = \sin\theta_i \pm \frac{q}{k_i} \tag{31c}$$

$$E_2 = +a t'(\theta_t) \sqrt{I_o} \; K_2 e^{i\omega x} e^{-ik_i R_o} e^{-ink_i h_2} \sum_{j=0}^{N} u_j j(q, y = -h) \sin(v_j q t) \tag{32a}$$

$$K_2 = k_1 (n\cos\theta_t - \cos\theta_i) \left[ \frac{(1+r(\theta_i)) n\cos\theta_t + (1-r(\theta_i))\cos\theta_i}{4\cos\theta_i} + \frac{q(1+r(\theta_i))(n\sin\theta_t + \sin\theta_i)}{4 k_1 \cos\theta_i (n\cos\theta_t - \cos\theta_i)} \right] \tag{32b}$$

$$\sin\theta_{t\pm1} = \frac{1}{n} \sin\theta_i \pm \frac{q}{n k_i} \tag{32c}$$

$$h_2 = \frac{2h}{\cos\theta_{t\pm1}} \tag{32d}$$

$$E_3 = +a t(\theta_i) \sqrt{I_o} \; K_3 e^{i\omega x} e^{-ik_i R_o} e^{-ink_i h_3} \sum_{j=0}^{N} u_j j(q, y = -h) \sin(v_j q t) \tag{33a}$$

$$K_3 = k_i(\cos\theta_t - n\cos\theta_{rfr}) \left[ \frac{(1 + r'(\theta_{rfr}))\cos\theta_t' + n(1 - r'(\theta_{rfr}))\cos\theta_{rfr}}{4\cos\theta_{rfr}} + \frac{q(1 + r'(\theta_{rfr}))(\sin\theta_t' + n\sin\theta_{rfr})}{4k_i\cos\theta_{rfr}(\cos\theta_t' - n\cos\theta_{rfr})} \right] \quad (33b)$$

$$\sin\theta_{t\pm1}' = n\sin\theta_{rfr} \pm \frac{q}{k_i} \quad (33c)$$

$$h_3 = \frac{2h}{\cos\theta_{rfr}} \quad (33d)$$

$$\theta_{rfr} = \sin^{-1}\left(\frac{1}{n}\sin\theta_i\right) \quad (33e)$$

$$E_4 = +at(\theta_i)_r'(\theta_d') \sqrt{I_o}\ K_4 e^{i\omega t} e^{-ik_1 R_o} e^{-ink_1 h_4} \sum_{j=0}^{N} u_y{}^j(q, y = 0)\sin(v_j q t) \quad (34a)$$

$$K_4 = nk_i(\cos\theta_d' + \cos\theta_{rfr}) \left[ \frac{n\cos\theta_d'}{2\cos\theta_{rfr}} \pm \frac{q(\sin\theta_d' + \sin\theta_{rfr})}{2k_i\cos\theta_{rfr}(\cos\theta_d' + \cos\theta_{rfr})} \right] \quad (34b)$$

$$\sin\theta_{d\pm1}' = \sin\theta_{rfr} \pm \frac{q}{nk_i} \quad (34c)$$

$$h_4 = \frac{h}{\cos\theta_{rfr}} + \frac{h}{\cos\theta_{d\pm1}'} \quad (34d)$$

Here, j runs from 0 to N and represents the mode solutions for j>0 and the dc term for j=0 (ie. $v_o=0$). Also, t is the transmission coefficient for passage from the air into the film, and t' is the transmission coefficient for passage from the film into the air. Finally, in these expressions the small-argument expansion of the Bessel function ($J_1(x) \sim x/2$ for $x \ll 1$) has been used since the rippled amplitude (as estimated in section IV) times the grating wavevector magnitude is small compared to one for all excitation geometries investigated in this experiment.

The signal intensity can be written as the square of the sum of the four electric fields given in eqs. (31–34). The resulting intensity will exhibit varying interference effects depending on the probing angle and wavelength, the index of refraction and thickness of the film, and the grating excitation wavevector. For the purpose of analyzing the relative intensities of the various pseudo-Rayleigh modes in an ISTS experiment, the only important interference occurs between the E-fields derived from the surface ripple ($E_1$–$E_3$) and the field derived from the interface ripple ($E_4$). Such interference can cause a mode with a large surface corrugation amplitude to only appear as a weak Fourier component in the experimentally measured diffraction signal and vice-versa. The final ISTS intensity (I) can be written in a manner which emphasizes this effect as $$I = I_o \left[ \sum_j [(F(n, h, k_i, q, \theta_i) u_y{}^j(q, y = -h) + G(n, h, k_i, q, \theta_i) u_y{}^j(q, y = 0))\sin(v_j q t)] \times c.c. \right] \quad (35)$$

where F and G are functions determined by summing terms in equations (31–34). This expression was obtained by averaging over an optical cycle with the assumption that acoustic terms are constant over this interval. It can be seen that, in general, the measured signal consists of a dc term, a series of heterodyned components oscillating at the pseudo-Rayleigh mode frequencies which arise from a beating against the dc term, and terms oscillating at sums and differences of the normal mode frequencies.

C. Qualitative Considerations

The relative intensities of the various modes seen with ISTS depend on two factors—the extent to which the different modes are excited by the pump pulses and the efficiency with which the surface and interface mode displacements diffract the probe pulse. Both of these factors can be quantified at a particular qh value by solving the full matrix eq. (16) for each mode. This was done using the elastic constants found for the Pyralin/silicon system as described below. Aside from an arbitrary laser-intensity dependent constant factor, the only additional input parameter needed to perform this computation was the Pyralin absorption coefficient $\zeta$. This was measured to be 1.3 $\mu m^{-1}$ using a Pyralin film coated onto a fused silica substrate. FIG. 10 shows the results of the calculations at qh=2.5. This figure shows material displacements for the first eight modes that exist at this value of qh. The relative excitation efficiencies for the different modes are indicated by the relative amplitudes A. (A=1 for the mode with the largest displacements.) The surface ripple amplitude relative to the maximum amplitude for each mode is given by R. Modes with large values of the produce AR contribute most to ISTS signal. There are several guidelines that can be determined through a study of these and other figures that allow for an understanding of the level of excitation and the resulting diffraction efficiency of a particular mode. First, modes with fewer spatial modulations along the y direction are excited more strongly than those with many nodes along y. This is reasonable since the heating excitation mechanism will tend to displace material in only one direction for a give value of z. Next, lower velocity modes in general have larger peak displacements than high velocity modes. This is due to the fact that as the mode velocity is increased and approaches the substrate transverse velocity, the mode displacements become spread out over both the film and far into the substrate. This leads to small peak displacement amplitudes compared to those of the low-velocity modes whose displacements are well localized in the film. Finally, it is evident that some modes involve much more surface and interface ripple than others. Since detection results predominantly from diffraction from surface and interface ripple, only modes with significant surface displacements along y are detected. With these guidelines, it is possible to qualitatively explain relative signal amplitudes from the various modes over a wide range of qh. For purposes of data analysis, the calculations provide a clear indication of which modes in a thin film are likely to be observed in ISTS data. In most of the data, only one or two frequency components are observed predominantly. Dispersion curves like those in FIG. 8 can be fit to the frequency values determined from the data, which the elastic moduli as adjustable parameters to be deduced from the best fit. To do this correctly it is essential to know which modes are under observation, i.e. which of the many dispersion curves should be fit to the experimentally determined frequency values. Another qualitative consideration that explains why ripple amplitude is small for modes with large velocities (which explains drop off for modes at a given qh and for all modes as qh is decreased to small values) is that modes are fast because they involve substantial motion in the substrate which is very stiff compared to the film (i.e. it is motion in the substrate that "speeds the mode up"). Since the substrate is very stiff, equal energy deposition will result in smaller displacements for fast modes.

FIG. 10 illustrates bulk and surface ripple amplitudes for a single value of wavevector q, given the film thickness h. FIG. 11 is a three-dimensional plot showing the calculated film surface ripple (the product AR) excited through ISTS as a function of qh and velocity for the various modes in 1 μm film. FIG. 12 displays the analogous results for the interface ripple. The x-y plane of these figures shows the mode velocity dispersion as in FIG. 8, while the z axis shows the relative ripple displacements for a given energy density of the ISTS excitation pulses. Note that since the displacements associated with each pseudo-Rayleigh mode are different, the relative ripple displacements for the film surface and the film—substrate interface are also different. Both, however, exhibit the same general trend of decreasing ripple amplitude with increasing qh. For fixed h as in this simulation, this corresponds to decreasing mode displacement amplitude with increasing wavevector which, as discussed earlier, is expected for ISTS excitation. In addition to this decrease in amplitude which is approximately like 1/q for values of qh above 1, there is a distinct decrease in the magnitude of the surfaces ripple for small values of qh. This decrease is attributed to the fact that as q is decreased to values near zero, even the lowest modes take on large velocities. Thus, as discussed above, these modes are not well localized and so have small peak displacements. For this reason, the ripple due to such modes is small.

In addition to the decrease in surface ripple at both high and very low values of q, it is seen in FIG. 11 that there is a "cross-over" near qh=1.5 where, upon increase in qh, the surface ripple due to mode two becomes small and that due to mode one becomes large. This occurs because the character of these two modes switch in this region. This "cross-over" is evident from the dispersion curves of FIG. 14, in which there is an "avoided crossing" of the first two frequencies, and through a comparison of modes one and two at qh=2.5 given in FIG. 10 and at qh=0.8 given in FIG. 13. (The presence of this cross over effect is a property of ripple phenomena.)

The relative contribution of each pseudo-Rayleigh mode to ISTS signal can be calculated using eq. (16) and the ripple information contained in FIGS. (11–12). The resulting mode intensity ratios can then be compared to the ratios found in the raw ISTS data for each value of qh and h. When the interface displacements are not negligibly small compared to the surface displacements, interference effects between these two contributions to diffracted signal become important so that with different experimental conditions—such as probe angle of incidence or film thickness—ISTS data can show vastly different mode intensity ratios (cf. eq. 35). Conversely, when one or the other set of displacements dominates, interference effects can be ignored and the resulting mode intensity ratios become independent of the precise experimental conditions and mimic the behavior of the relevant ripple displacements. From FIGS. (11–12) it is clear that the theoretical surface displacements are over an order of magnitude larger than the interface displacements for the two lowest velocity modes with qh values above ~0.5, while for the other modes and at lower qh, the surface and interface displacements are of the same order. Calculations performed at other film thicknesses between 1 and 5 μm show this same general behavior. Thus, for the samples examined in this study, one would expect the relative intensities of the two lowest modes to mirror the relative intensities shown in FIG. 9 for qh>0.5. (An analysis of the complete mode intensity spectrum requires the full solution of eq. (35).)

D. Quantitative Analysis of ISTS Data

As stated earlier, the dc term dominates the ISTS signal for these experiments. In fact the power in the zero-frequency peak of the Fourier transforms ranged from 30 to 200 times greater than the acoustic peaks. Thus, the heterodyne terms in equation (35) dominate and the frequencies of the most intense Fourier peaks will correspond to the fundamental pseudo-Rayleigh mode frequencies $\omega_j$.

The values of $\omega_j$ found for all the scattering wavevectors and sample thicknesses in this study were converted to phase velocities and plotted versus qh. The results are showing in FIG. 14. In cases where multiple modes were excited, only those with Fourier transformed intensities greater than half that of the largest were plotted. In addition, to eliminate the possibility of spurious peaks due to sample imperfections, data points were taken at several spots on each sample and only frequencies that were consistent from spot to spot on the same were kept. The estimated experimental uncertainties for the velocities range from 1% at the highest qh values to 5% at the lowest qh values observed for each sample. The qh values are accurate to ±0.1. The main source of error results from uncertainties in the scattering wavevector which are derived from uncertainties in the mechanical measurement of the scattering angle. This error can be substantially reduced by deducing the scattering wavevector directly from ISTS data taken with a well characterized reference sample.

The solution for the pseudo-Rayleigh mode dispersion for this system requires the density and the longitudinal and transverse velocities for both the silicon and the Pyralin as inputs. For silicon, $\rho_s$=2.33 g/cm and the isotropic velocities are '$L_s$=8945 m/s and '$T_s$=5341 m/s. For Pyralin, the values given by Dupont for the density and Young's modulus (Y) are 1.45 g/cm$^3$ and 2.4 GPa respectively.[22] To the inventor's knowledge, there is no reported measurement of Poisson's ration (v) for this film. All three of these values are necessary to obtain the longitudinal and transverse velocities for the film according to eqs. (36) and (37).

$$v_T^2 = \frac{Y}{2\rho(1+v)} \tag{36}$$

$$v_L^2 = \frac{Y}{\rho(1+v)} \left[ 1 + \frac{v}{1-2v} \right] \tag{37}$$

Different sets of dispersion curves were generated by solving eq. (25) using the silicon and Pyralin parameters given above and varying Poisson's ration for Pyralin from 0 to 0.5. None of these theoretical data sets were able to fit the experimental data adequately. The experimental data was thus fit numerically using the Marquardt-Levenberg nonlinear least squares algorithm and allowing all three of the Pyralin parameters to vary. In performing such a calculation, one must assign each experimental point to a particular dispersion curve. This was fairly straightforward for the data shown in FIG. 14 since the experimental points group together into well-defined curves resembling the pseudo-Rayleigh dispersion curves. The theoretical results shown in FIGS. 11 and 12 and discussed above indicate that the lowest velocity pseudo-Rauleigh modes should give rise to the strongest signals for most of the wavevectors used. It was therefore assumed that the two lowest-velocity sets of data points correspond to the two lowest-velocity pseudo-Rayleigh dispersion curves. The Pyralin velocities ('Lf and "Tf) parameters were adjusted to fit the points on these lowest-velocity curves with the density fixed at the measured value of 1.45 g/cm³. FIG. 14 shows the data points and the fit. Using the values obtained, the other pseudo-Rayleigh dispersion curves were calculated and plotted on FIG. 14. The agreement between these higher-velocity pseudo-Rayleigh dispersion curves and the higher-velocity data points is excellent, with no further adjusting of any parameters.

The Pyralin velocity parameters determined from the fit are 'Lf=2650 m/sec and "Tf=1160 m/sec. While it is never certain that the global minimum in the value of $\chi^2$ using nonlinear least squares fitting routines is reached, these values correspond to the lowest minimum found after starting from many different initial guesses for the parameter values. Varying either of the Pyralin velocity parameters by 10% led to substantially worse fits. Varying the substrate parameters by the same amount led to worse fits for values of qh<1, but did not affect the quality of the fits at higher qh values. It is thus estimated that the overall uncertainties in the pyrlain velocity parameter values to be ±5%.

The relative intensities of the two lowest modes can be compared to the film surface displacements of FIG. 11 for qh>0.5. Experimentally, FIG. 14 shows that at least one of these two modes is present for all the samples. According to FIG. 9, the second lowest mode should dominate from qh~0.5 to qh~1.5 while at higher qh values, i.e. above the crossover discussed earlier, the lowest mode should have a higher intensity. Upon examination of FIG. 12, this qualitative behavior definitely obtains since, for all the samples, the density of observed data points is much higher for the second mode than for the first qh values less than the crossover, while at higher qh values the only observed data points correspond to the first mode. A quantitative mode intensity analysis is possible by accurately fixing or measure the probe angle of incidence $\theta_i$ since, according to eqs (29–34), changes in $\theta_i$ significantly change the values of F and G in eq. (35) which in turn can change the final mode intensities seen in an ISTS experiment.

The outlying high velocity data points observed are not strictly pseudo-Rayleigh surface modes but rather represent modes which arise from interactions with the free substrate boundary. Their counterparts for the semi-infinite substrate are known as "leaky" modes which are damped due to the fact that they lose energy to the semi-infinite substrate as they propagate. The behavior of the modes can be elucidated by treating the finite size of the substrate explicitly. This is demonstrated below.

The solution for the transient grating excitation of a thin film coating is generalized to include the effects of a substrate with finite thickness. The formal solution for the displacement potentials is still given by eqs. (13–14). However, now the finite substrate has a free boundary at y=H (cf. FIG. 7) which is ignored for the semi-infinite system. For this reason, the $C_\phi$ and $C_\psi$ terms of eq. (13–14) are no longer unphysical and must be retained in order that the normal components of the stress at this new surface can be fixed to zero.

With the two new boundary condition equations and the two new unknown potential constants, eq. (16) becomes an 8×8 matrix equation. Using the Duhamel-Neumann expression for the stress (eq.) 15), and assuming as before that there is no heating of the silicon, it can be shown that the new matrix equation takes the form $$C^f D^f = F^f \tag{38}$$

where $$C = \tag{39}$$

$$\begin{pmatrix}
(1+p^2)e^{-nkh} & (1+p^2)e^{nkh} & 2ipe^{-pkh} & -2ipe^{pkh} & 0 & 0 & 0 & 0 \\
2ine^{-nkh} & -2ine^{nkh} & -(1+p^2)e^{-nkh} & -(1+p^2)e^{nkh} & 0 & 0 & 0 & 0 \\
1+p^2 & 1+p^2 & 2ip & -2ip & -(1+r^2)g & 2irg & -(1+r^2)g & -2irg \\
2in & -2in & -(1+p^2) & -(1+p^2) & 2img & (1+r^2)g & -2img & (1+r^2)g \\
-1 & -1 & -ip & ip & 1 & -ir & 1 & ir \\
in & -in & -1 & -1 & im & 1 & -im & 1 \\
0 & 0 & 0 & 0 & -g(1+r^2)e^{-mkH} & 2igre^{-rkH} & -g(1+r^2)e^{mkH} & -2igre^{rkH} \\
0 & 0 & 0 & 0 & 2igme^{-mkH} & g(1+r^2)e^{-rkH} & -2ime^{mkH} & g(1+r^2)e^{rkH}
\end{pmatrix}$$

$$D = \begin{pmatrix} A_\phi \\ B_\phi \\ A_\psi \\ B_\psi \\ D_\phi \\ D_\psi \end{pmatrix} \tag{40}$$

$$\begin{pmatrix}
\dfrac{-(\delta(k)+\delta(k-q))}{k^2} + \dfrac{v_{Lf}^2}{k^2}\left(\dfrac{-(v_{Lf}^2-2v_{Tf}^2)}{v_{Lf}^2} + \dfrac{\zeta^2}{k^2}\right) & \left(\dfrac{\delta(k)}{v^2+\dfrac{v_{Lf}^2\zeta^2}{k^2}} + \dfrac{\delta(k-q)}{v^2+v_{Lf}^2\left(\dfrac{\zeta^2-k^2}{k^2}\right)}\right) \\
\dfrac{2\zeta v_{Tf}^2}{ik^3}\left(\dfrac{\delta(k)}{v^2+\dfrac{v_{Lf}^2\zeta^2}{k^2}} + \dfrac{\delta(k-q)}{v^2+v_{Lf}^2\left(\dfrac{\zeta^2-k^2}{k^2}\right)}\right)
\end{pmatrix} \tag{41}$$

$$F = \frac{iA\gamma}{v_{Tf}^2 \rho k v} \left| \begin{array}{c} \frac{-e^{-\zeta d}(\delta(k) + \delta(k-q))}{k^2} + \frac{e^{-\zeta d}v_{Lf}^2}{k^2}\left(\frac{-(v_{Lf}^2 - 2v_{Tf}^2)}{v_{Lf}^2} + \frac{\zeta^2}{k^2}\right)\left(\frac{\delta(k)}{v^2 + \frac{v_{Lf}^2 \zeta^2}{k^2}} + \frac{\delta(k-q)}{v^2 + v_{Lf}^2\left(\frac{\zeta^2 - k^2}{k^2}\right)}\right) \\ \frac{2e^{-\zeta d}\zeta v_{Tf}^2}{ik^3}\left(\frac{\delta(k)}{v^2 + \frac{v_{Lf}^2\zeta^2}{k^2}} + \frac{\delta(k-q)}{v^2 + v_{Lf}^2\left(\frac{\zeta^2 - k^2}{k^2}\right)}\right) \\ \frac{-e^{-\zeta d}v_{Tf}^2}{k^2}\left(\frac{\delta(k)}{v^2 + \frac{v_{Lf}^2\zeta^2}{k^2}} + \frac{\delta(k-q)}{v^2 + v_{Lf}^2\left(\frac{\zeta^2 - k^2}{k^2}\right)}\right) \\ \frac{e^{-\zeta d}v_{Tf}^2}{k^3}\left(\frac{\delta(k)}{v^2 + \frac{v_{Lf}^2\zeta^2}{k^2}} + \frac{\delta(k-q)}{v^2 + v_{Lf}^2\left(\frac{\zeta^2 - k^2}{k^2}\right)}\right) \\ 0 \\ 0 \end{array} \right|$$

Information is extracted from this matrix equation with the same techniques that were used for the 6×6 equation in the main text. The resulting dispersion curves for the thirty lowest velocity modes of a system composed of 3 μm Pyralin film on a 330 μm silicon substrate are showing in FIG. A1. One can see that relaxing the semi-infinite substrate assumption give rise to extra plate modes propagating predominantly within the substrate with velocities above the substrate transverse velocity 'T$_s$ which was, in the semi-infinite case, the cutoff for propagating modes of the system. The dispersion curves for velocities sufficiently below the 'T$_s$ are almost identical to those for the pseudo-Rayleigh modes calculated using the semi-infinite substrate system and shown in FIG. 14. The only differences occur at phase velocities near the cut-off and, for the lowest velocity mode, at very low (<0.2) qh values. This behavior is expected and confirms that the semi-infinite substrate approximation is adequate to explain nearly all of the pseudo-Rayleigh modes seen in these experiments.

The extra plate modes above 'T$_s$ are produced as a result of acoustic reflections from the free substrate surface. They can be obtained within the semi-infinite substrate approximation as well, but only as "leaky" modes with finite lifetime due to energy flow into the infinite substrate. The existence of these modes for the Pyralin/silicon system used in these experiments provides an explanation for the ISTS data points occurring above 'T$_f$ in FIG. 14.

E. Discussion

The values of 'Lf=2650±130 m/sec and 'Tf=1160±60 m/sec deduced in this study for Pyralin 2555 combined with the density of 1.45 g/cm$^3$ correspond to a Young's modulus of 5.4±0.5 GPa and a Poisson's ratio of 0.38±0.02. (The uncertainties given for Young's modulus and the Poisson ratio are calculated from the uncertainties for 'Lf and 'Tf determined from the study above and do not account for uncertainties in the film density.) To the inventor's knowledge, this represents the first measurement of Poisson's ratio in this material. This value for Young's modulus is over 100% higher than the previously measured value of 2.4 GPa. The value of Young's modulus can depend very sensitively on the method of film curing. Thus, the difference is believed due to intrinsic difference in sample characteristics.

Polyimide films can exhibit variation in the degree of chain orientation and in density as a function of depth. These measurements yield values which are averaged over the film thickness and so do not provide direct information about depth dependencies. Measurements of thinner films may yield different parameters, indicative of differences in film properties very close to the substrate surface. By tilting the grating wavevector so that it has a component perpendicular to the film, it is possible to determine separate in-plane and out-of-plane elastic moduli. The theoretical treatment outlined here could be generalized to take this into account.

In general, there are several different protocols available for extracting the elastic parameters from ISTS data on thin supported films. One method, which was demonstrated above, involves determining the mode velocities at a range of qh values—by either changing scattering angle or sample thickness or both—and then varying the elastic parameters until a good match between theoretical dispersion curves and data is obtained. Experimental error can be reduced with improved accuracy of the scattering wavevector measurement and an analysis along these lines with fewer qh values and higher accuracy can be achieved. An alternative or complementary method involves using the relative ISTS signal intensity information obtained for the different modes at each qh values. As discussed, a quantitative analysis of the relative intensities requires accurate specification of the incident probe angle, the indices of refraction of the film and substrate, and the film thickness. The first parameter is easily determined in the ISTS experiment. The indices of refraction and film thickness can be measured by other techniques, or treated as free parameters in a fitting scheme. The elastic parameters may be extracted using data from only one qh value at which multiple modes are observed, by fitting both the pseudo-Rayleigh mode velocities and relative intensities. With efficient computing algorithms to accomplish fitting, the elastic parameters may be extracted with the same real-time rates demonstrated for the data acquisition. Generally, the experiment can be optimized with an improved probe pulse temporal profile.

E. Determination of Adhesion Quality

In the analysis described above, the film and substrate were modeled such that together they form an acoustic waveguide and together determine the frequencies of the acoustic waveguide modes that propagate in the film-substrate system. Referring to FIGS. 16 and 16a, comparing the dispersion curves for a tightly bound film-substrate system with a system in which the substrate is removed (which would be equivalent to a film-substrate system with a substrate that has a very low stiffness) it is seen that the waveguide frequencies change dramatically. These changes can be used to detect regions where the film has become debound from the substrate by sampling the film at various locations.

Further, the degree of film substrate adhesion can be determined. For example, the absence of a substrate is equivalent to the case where the film is no longer stuck to the substrate. If the film is slightly stuck but not tightly bound, the acoustic waveguide frequencies are intermediate between the case where the substrate is present and where it is removed. By measuring the actual positions of the frequencies, the degree of adhesion can be determined. In the adhesion model, two parameters are introduced ($k_z$, $k_y$, further discussed below). One is a spring stiffness parameter per unit area for motions parallel to the plane of the film ($k_z$). The other is a spring stiffness parameter per unit area for motions perpendicular to the film ($K_y$). Although each parameter affects the waveguide frequencies, for films with intermediate degrees of adhesion, we expect that since the film is in contact with the substrate, the stiffness parameter ($k_y$) for motions perpendicular to the film will be large (i.e. close to the tightly bound case). Referring to FIG. 17 only the stiffness parameter for motions parallel to the plane ($k_z$) of the film has been varied. (The plot wherein $k_z$=infinity corresponds to the tightly bound case, FIG. 16, and the case wherein $k_z$=0 corresponds to the case of a film on a frictionless surface.) As can be seen from this figure, there is a smooth variation in the acoustic waveguide mode frequencies between the tightly bound case and the frictionless interface case (i.e. the case where there is no resistance to film motions parallel to the plane of the film but there is resistance to motions perpendicular to the film). The waveguide frequencies are most sensitive to changes in the adhesion at small wavevector times thickness values. Therefore, this region can be probed (by varying the wavevector of the excitation). The plots in FIGS. 16 and 17 were generated by computer algorithm using inputs as follows.

$$\Theta_{yy}(d^+) - \Theta_{yy}(d^-) \tag{42}$$

$$\Theta_{yz}(d^+) = \Theta_{yz}(d^-) \tag{42a}$$

$$[u_z(d^+) - u_z(d^-)] k_z - \frac{1}{2} (\Theta_{yz}(d^+) + \Theta_{yz}(d^-)) = 0 \tag{42b}$$

$$[u_y(d^+) - u_y(d^-)] k_y - \frac{1}{2} (\Theta_{yy} + \Theta_{yy}) = 0 \tag{42c}$$

where $J_{ij}$ is the stress tensor; $u_i$ is the displacement vector; $k_z$ is an elastic stiffness/unit area for motion along the z axis; $k_y$ is an elastic stiffness/unit area for motion along the y axis to determine acoustic mode dispersion and excitation efficiency. (Discussion of models for a different purpose can be found in F. J. Margetan et al., *Journal of Nondestructive Evaluation*, Vol. 7, Nos. 3 and 4, 1988, p. 131.)

An inertial mass term was used to describe excess mass at the crack is dropped for the adhesion model.

F. Analysis of Thermal Diffusion Data

Referring to FIG. 18, the following is a derivation of a technique for measurement of thermal diffusion, using boundary conditions for a thin film. Starting with the equation of motion:

$$\frac{\partial^2 T}{\partial y^2} + \frac{\partial^2 T}{\partial z^2} - \frac{c\rho}{\kappa} \frac{\partial T}{\partial t} = -\frac{Q}{\kappa} \tag{43}$$

Q represents the heat source; K is the thermal conductivity; C is the heat capacity per unit mass; and $\rho$ is the density.

It is assumed that heat flow occurs within the film and out of the film into the air and substrate. The heat flow out of the film obeys Newton's laws of heat propagation (i.e. heat flow is proportional to the temperature gradient leaving the following boundary conditions on heat flow:

$$\left. \frac{\partial T}{\partial y} \right|_{y=0} = hT \tag{44}$$

$$\left. \frac{\partial T}{\partial y} \right|_{y=d} = h'T$$

In the above, the z axis is in the plane of film and the y axis parallel to the film thickness with the origin, y=0, of the film surface and where the film thickness is y=d, h and h' relate to the degree of thermal coupling between the film and air and film and substrate, respectively. For ISTS excitation:

With $Q=A(1+e^{iqz})(e^{-\zeta y}Y)\gamma(t)$, the transformed solution (using transforms above (see page 29)) is:

$$T(s, k, y) = B(s, k)\exp\left\{ -y\left( k^2 + \frac{c\rho s}{\kappa} \right) \right\} + \tag{45}$$

$$C(s, k)\exp\left\{ y\left( k^2 + \frac{c\rho s}{\kappa} \right) \right\}$$

$$-\frac{A}{k} e^{-\zeta y} \left[ \frac{\delta(k) + \delta(k-B)}{\zeta^2 - k^2 - \frac{c\rho s}{\kappa}} \right] \tag{46}$$

where A is the amplitude factor related to excitation pulse intensity and optical absorption coefficient, q is the wavevector and $\zeta$ is the optical absorption coefficient. Applying the boundary conditions and inverting the transform yields $$T(y,z,t) = \left[ 1 + \exp\left( \frac{-\kappa q^2}{c\rho} t \right) e^{i\beta z} \right] \sum_n \exp\left( \frac{-\kappa r_n^2}{c\rho d^2} t \right) F(y, r_n) \tag{47}$$

with $$\tan r_n = \frac{(h - h')r_n d}{h h' d^2 + r_n^2} \tag{48}$$

and $$F(y, r_n) = \frac{2A}{c\rho\left( \zeta^2 + \frac{r_n^2}{d^2} \right)} \left\{ \frac{(h + \zeta)\left( \frac{r_n}{d} \cos\frac{r_n(y-d)}{d} + h'\sin\frac{r_n(y-d)}{d} \right) - e^{-\zeta d}(h' + \zeta)\left( \frac{r_n}{d} \cos\frac{r_n y}{d} + h\sin\frac{r_n y}{d} \right)}{\left[ 2 - d(h' - h)\sin r_n + (h' - h)\left( \frac{d}{r_n} - d\cot r_n \right)\cos r_n \right]} \right\} \tag{49}$$

(perpendicular to the plane of the sample surface). These boundary conditions are used with the equations of motion In the quasi-static limit, the displacements are related to the temperature as follows:

$$\nabla^2 \phi = \alpha_T T \tag{50}$$

$$\vec{u} = \nabla\phi + \nabla \times \vec{\psi} \text{ with } \nabla \cdot \vec{\psi} = O \ \& \ \nabla^2\vec{\psi} = O \tag{50a}$$

where $\alpha_T$ is the coefficient of thermal expansion and $\vec{\mu}$ is the displacement.

In this limit, the temporal dependence of $\vec{\mu}$ is determined by the temporal dependence of T. Thus, the signal is a sum of exponentials with the same decay rate in equation (46). The different decay rates can be extracted with a linear prediction routine. With the rates determined in this manner, comparison can be made to theory to determine:

$$\frac{\kappa q^2}{c\rho} \ \& \ \frac{\kappa r_n^2 t}{c\rho} \tag{51}$$

by changing q and d, then, predictions can be made for the form of the experimental decay. In this way, equation (51) can be compared to experimental values to determine the accuracy of the calculated values.

Further Embodiments

It will be evident from the above that the invention enables many embodiments and advantages. While the experiments may be carried out on thin films to particular advantage as discussed above where surface ripple is the predominant phenomenon leading to diffraction of the probe, the ripple effect may also be induced on thicker samples. The experiment can be optimized to selectively analyze diffraction from ripple over diffraction from bulk, refractive index modification. The ripple effect can be preferentially detected by maximizing the amount of reflected light by increasing the incident angle of the probe beam. The optimum incident angle may be determined based on sample thickness and the refractive index to enable a large incident angle while avoiding substantial losses due to total internal refraction. The detection of diffraction from the ripple effect can also be optimized on freestanding samples by detection of transmitted and reflected probe radiation and subtracting the former, which contains bulk-properties information, from the latter, which contains ripple information. (It will also be understood that for thin films, ripple from both sides of a film can be detected, even for films on a substrate, in which case ripple of the sample-substrate interface can be detected.) The presence of signal induced from bulk properties can also be detected by study of the polarization of the diffracted beam. A polarizer can be positioned after the probe focusing optic (e.g. optic 54) and another polarizer positioned before the detector (e.g. detector 58). As discussed above bulk properties vary the incident polarization. The polarization can be studied as a function of incident angle to determine the optimum angle for detecting ripple induced diffraction. Further, the excitation radiation can be optimized to enhance the diffraction signal arising from ripple. The wavevector dependence of the signal can be studied (e.g. with a computer) to determine that the diffraction signal is predominately from ripple. Generally, a smaller excitation wavevector (longer excitation wavelength or smaller angle of incidence of the excitation beams) enhances the ripple effect. In the experiments on the sample as described above, the maximum wavevector for which signal was obtained was about $q=1.81 \ \mu m^{-1}$. Larger maximum wavevectors can be used if a less stiff sample or higher intensity probe laser is used.

Other embodiments are within the scope of the following claims.

What is claimed is:

1. An apparatus for measuring the properties of a sample of material, comprising:

a first, excitation source for producing excitation radiation adapted to impinge upon said sample of material, said excitation radiation comprising radiation composed of at least two component beams which interfere within said sample, each incidence of interference of said excitation radiation being sufficient to induce transient phonons in said material which give rise to a transient, time dependent periodic ripple morphology of alternating peaks and valleys on a surface of said sample, a detection system for detecting said ripple morphology by diffraction of radiation including:

a second, probe source for producing probe radiation arranged to be diffracted by the periodic ripple morphology on the surface of said sample to form a diffraction signal which emerges on the same side of said sample as said probe radiation, a detector for detecting the diffraction signal from said probe source radiation diffracted by said surface ripple morphology, and an analyzer for selectively analyzing said diffraction signal formed by said transient ripple morphology.

2. The apparatus of claim 1 wherein said probe source produces radiation that is not substantially absorbed by said sample.

3. The apparatus of claim 1 wherein said probe source produces radiation that is absorbed about 10% or less than said radiation from said excitation source.

4. The apparatus of claim 3 wherein said probe source produces radiation that is absorbed about 1% or less than said radiation from said excitation source.

5. The apparatus of claim 1 wherein said excitation source radiation comprises ultraviolet radiation absorbed sufficiently by said sample to induce heating that gives rise to said phonons and ripple morphology.

6. The apparatus of claim 5 wherein said probe source radiation comprises visible radiation not substantially absorbed by said sample.

7. The apparatus of claim 1 wherein said sample comprises a thin sample of about 500 μm or less.

8. The apparatus of claim 7 wherein said thin sample is about 10 μm or less.

9. The apparatus of claim 1 wherein said sample comprises a thin polymeric film.

10. The apparatus of claim 9 wherein said film comprises a free-standing film.

11. The apparatus of claim 9 where said film is disposed on a support.

12. The apparatus of claim 1 wherein said analyzer includes a polarizer for determining change of polarization of said probe beam after diffraction from said surface to selectively analyze diffraction from said ripple morphology.

13. The apparatus of claim 1 wherein said analyzer is for analyzing said signal as a function of the wavevector and to selectively analyze diffraction signal from said ripple morphology.

14. The apparatus of claim 1 further including a probe beam and detector constructed for detecting and resolving a substantial time-portion of the time-dependent diffraction induced by each incidence of interference of said excitation radiation.

15. The apparatus of claim 14 wherein said excitation radiation is pulsed radiation and, said probe radiation is of a selected pulse width and said detector is adapted to detect the diffraction signal for the duration of said probe pulse.

16. The apparatus of claim 15 wherein said detector is constructed to detect the entire detectable diffraction signal induced by each excitation pulse.

17. The apparatus of claim 16 wherein said excitation radiation has a pulse width on the order of psec duration and the probe radiation pulse width is on the order of nsec duration.

18. The apparatus of claim 17 wherein said detector has a time resolution on the order of 1 nsec.

19. The apparatus of claim 14 wherein said probe pulse has a peak power output of about 1000 watts or greater.

20. The apparatus of claim 19 wherein said laser comprises a Q-switch YAG laser.

21. The apparatus of claim 14 wherein said excitation pulse is generated from a pulsed laser and said probe pulse is generated from a CW laser.

22. The apparatus of claim 1 including an analyzer adapted for determining from said diffraction signal the adhesion of said sample on a substrate surface.

23. The apparatus of claim 1, wherein the sample of material is a thin film, and the analyzer selectively analyzes the diffraction signal to determine the thickness of the thin film.

24. The apparatus of claim 23, wherein the thin film is opaque to the excitation radiation.

25. A method for measuring the properties of a sample comprising:

impinging a pulse of excitation radiation upon said sample, said excitation radiation being composed of at least two component beams which interfere within said sample, and being selected such that each incidence of said interference is sufficient to induce transient phonons in said sample which give rise to a transient, time dependent ripple morphology of alternating peaks and valleys on a surface of said sample, detecting said ripple morphology by diffraction of probe radiation from said surface having the periodic ripple morphology to form a diffraction signal which emerges on the same side of said sample as said probe radiation, and selectively detecting the diffraction signal diffracted by said ripple morphology.

26. The method of claim 25 wherein said sample is about 500 μm thick or less.

27. The method of claim 26 wherein said sample is about 10 μm thick or less.

28. The method of claim 27 wherein said sample is a pure polymer sample.

29. The method of claim 28 comprising selecting excitation radiation that is absorbed by the sample.

30. The method of claim 29 comprising selecting probe radiation that is absorbed less than said excitation radiation.

31. The method of claim 30 comprising selecting probe radiation that is not substantially absorbed by said sample.

32. The method of claim 31 wherein said excitation radiation comprises UV radiation and said probe radiation comprises visible radiation.

33. The method of claim 25 comprising detecting and resolving a substantial time-portion of the diffraction signal induced by each incidence of interference of said excitation radiation.

34. The method of claim 33 wherein said probe source is a CW laser.

35. The method of claim 33 further comprising:

providing a probe source having a peak power output of about 1000 watts or greater, and detecting and resolving a substantial time-portion of the time-dependent diffraction induced by each excitation pulse.

36. The method of claim 33 further including signal averaging the diffracted radiation from multiple excitation pluses.

37. The method of claim 25 further comprising analyzing said signal to selectively analyze diffraction from said ripple.

38. The method of claim 35 comprising analyzing the polarization of said diffracted radiation.

39. The method of claim 37 comprising analyzing the diffracted radiation as a function of wavevector.

40. The method of any one of claims 36 to 38 including optimizing the diffraction from said ripple by varying the angle of incidence of said probe beam.

41. The method of any one of claims 36 to 38 including optimizing the diffraction from said ripple by varying the wavelength or angle of incidence of said excitation radiation.

42. The method of claim 25 further comprising determining from said diffraction signal the adhesion of said sample on a substrate surface.

43. The method of claim 37, wherein the sample of material is a thin film, and during the analyzing step the diffraction signal is selectively analyzed to determine the thickness of the thin film.

44. The method of claim 43, wherein the thin film is opaque to the excitation radiation.

45. An apparatus for measuring the properties of a thin sample of polymeric material comprising:

a first, excitation laser source for producing a pulse of radiation adapted to impinge upon said sample, said excitation source comprising radiation composed of at least two component pulses which interfere within said thin film, said excitation radiation adapted to induce transient phonons in said material which give rise to a transient, time-dependent periodic ripple morphology of alternating peaks and valleys on a surface of said sample, a detection system for detecting said ripple morphology by diffraction of radiation including:

a second, probe laser source for producing radiation, said probe radiation being of selected wavelength not substantially absorbed by said sample and arranged to be diffracted by the periodic ripple morphology on the surface of said sample to form a diffraction signal which emerges on the same side of said sample as said probe radiation, and a detector for detecting the diffraction signal.

46. The apparatus of claim 45 further including a probe beam and detector constructed for detecting and resolving a substantial time-portion of the time-dependent diffraction induced by each excitation pulse.

47. The apparatus of claim 46 further including a signal averager for signal averaging said diffraction signals arising from repeated excitation and probing of said sample.

48. The apparatus of claim 46 wherein said excitation pulse is on the order of psec duration and the probe is pulsed radiation with a pulse on the order of nsec duration.

49. The apparatus of claim 48 wherein the probe laser source peak power is about 1000 watts or more.

50. The apparatus of claim 49 wherein the peak power is about 10,000 watts.

51. The apparatus of claim 49 wherein said laser is a YAG Q-switched laser.

52. The apparatus of claim 51 wherein said detector has a response time on the order of 1 nsec.

53. The apparatus of claim 45 wherein said diffracted radiation is reflected from the back surface of said sample opposite said radiation sources.

54. The apparatus of claim 45 wherein said probe source is a CW laser.

55. The apparatus of claim 54 wherein said probe source is a gated argon ion laser.

56. The apparatus of any one of claims 45 or 54 wherein said probe has a power output of around 1 watt.

57. The apparatus of claim 45 including an analyzer adapted for determining the adhesion of said polymer sample on a substrate surface from said diffraction signal.

58. The apparatus of claim 45 including an analyzer adapted for determining the thermal diffusion of said sample from said diffraction signal.

* * * * *